United States Patent
Chung

(10) Patent No.: US 10,620,062 B2
(45) Date of Patent: Apr. 14, 2020

(54) CEMENT-BASED MATERIAL SYSTEMS AND METHOD FOR SELF-SENSING AND WEIGHING

(71) Applicant: Deborah D. L. Chung, East Amherst, NY (US)

(72) Inventor: Deborah D. L. Chung, East Amherst, NY (US)

(73) Assignee: Deborah D. L. Chung, East Amherst, NY (US)

( * ) Notice: Subject to any disclaimer, the term of this patent is extended or adjusted under 35 U.S.C. 154(b) by 380 days.

(21) Appl. No.: 15/791,015

(22) Filed: Oct. 23, 2017

(65) Prior Publication Data
US 2019/0120707 A1    Apr. 25, 2019

(51) Int. Cl.
*G01L 1/14* (2006.01)
*G01N 33/38* (2006.01)
*G01N 27/22* (2006.01)

(52) U.S. Cl.
CPC ............ *G01L 1/146* (2013.01); *G01N 27/226* (2013.01); *G01N 33/383* (2013.01); *G01N 2203/003* (2013.01)

(58) Field of Classification Search
CPC .... G01L 1/146; G01N 27/226; G01N 33/383; G01N 2203/003
See application file for complete search history.

(56) References Cited

U.S. PATENT DOCUMENTS

| | | | | |
|---|---|---|---|---|
| 2,544,673 A | * | 3/1951 | Haber | G01L 1/2287 324/663 |
| 3,967,197 A | * | 6/1976 | Anderson | G01N 27/223 324/664 |
| 5,817,944 A | | 10/1998 | Chung | |
| 6,023,170 A | * | 2/2000 | Hilhorst | G01N 27/041 324/650 |
| 2007/0126433 A1 | * | 6/2007 | Theophanous | G01N 27/225 324/690 |

(Continued)

FOREIGN PATENT DOCUMENTS

| | | |
|---|---|---|
| EP | 2947456 A1 | 11/2015 |
| EP | 3115781 A1 | 1/2017 |

(Continued)

*Primary Examiner* — Nathaniel T Woodward

(57) ABSTRACT

This invention provides cement-based material system for the self-sensing of the force (compressive, tensile, flexural, shear, torsional, and combinations thereof) exerted on the cement-based material. It also provides cement-based material system for weighing and a method of the self-sensing. No particular admixture is required in the cement-based material. The measurement involves using two electrodes on the same surface of the cement-based material. The force to be sensed is exerted on the cement-based material, particularly on a part of the material surface between the electrodes. The capacitance measured between the two electrodes serves as an indicator of the force. This invention also provides a method of the self-sensing of force exerted on a cement-based material. The method involves positioning two electrodes on the cement-based material and measuring the capacitance between these electrodes while force is applied to the cement-based material, particularly on a part of the material surface between the electrodes.

20 Claims, 36 Drawing Sheets

(56) References Cited

U.S. PATENT DOCUMENTS

| | | | |
|---|---|---|---|
| 2009/0292427 A1 | 5/2009 | Yamada | |
| 2011/0238210 A1 | 9/2011 | Roekens | |
| 2011/0252715 A1 | 10/2011 | Aldraihem | |
| 2011/0252734 A1 | 10/2011 | Aldraihem | |
| 2013/0036821 A1 | 2/2013 | Belkerdid | |
| 2013/0106447 A1 | 5/2013 | Bridges | |
| 2014/0182848 A1 | 7/2014 | Roberson | |
| 2015/0175365 A1 | 6/2015 | Picard | |
| 2015/0276702 A1 | 10/2015 | England | |
| 2015/0338380 A1 | 11/2015 | Ziehl | |
| 2016/0054247 A1 | 2/2016 | Colosimo | |
| 2016/0201451 A1 | 7/2016 | Godager | |
| 2016/0243610 A1 | 8/2016 | Orsi | |
| 2016/0266086 A1 | 9/2016 | Von Herzen | |
| 2016/0340245 A1 | 11/2016 | Loh | |
| 2017/0016874 A1 | 1/2017 | Radjy | |
| 2017/0024033 A1 | 1/2017 | Chandran | |
| 2017/0160111 A1 | 6/2017 | Dowdall | |
| 2017/0269779 A1 | 9/2017 | Chan et al. | |
| 2017/0284996 A1* | 10/2017 | Ghods | G01N 17/04 |
| 2018/0238820 A1* | 8/2018 | Ghods | G01N 27/026 |
| 2019/0017365 A1* | 1/2019 | Roberson | G01B 7/18 |

FOREIGN PATENT DOCUMENTS

| | | |
|---|---|---|
| IN | 2014MU02525 A | 9/2014 |
| WO | WO2008094358 A1 | 8/2008 |
| WO | WO 2015118333 A1 | 8/2015 |
| WO | WO 2015150463 A1 | 10/2015 |
| WO | WO 2015178883 A1 | 11/2015 |
| WO | WO 2016019247 A1 | 2/2016 |
| WO | WO 2016148696 A1 | 9/2016 |
| WO | WO 2017011460 A1 | 1/2017 |
| WO | WO 2017030579 A1 | 2/2017 |

* cited by examiner

CEMENT-BASED MATERIAL SYSTEMS AND METHOD FOR SELF-SENSING AND WEIGHING

FIELD OF THE INVENTION

The present disclosure relates to the field of self-sensing cement-based materials. It also relates to the field of weighing.

BACKGROUND OF THE INVENTION

Weighing refers to the determination of the force that gravitation exerts upon an object. It is commonly achieved by using a balance, scale, or other mechanical device.

Weighing is needed in the manufacturing industry (e.g., for weighing the raw materials used in fabrication and the products of the fabrication), the goods delivery industry (e.g., for weighing the goods in a delivery truck), the asset control industry (e.g., for weighing the cargo in a cargo yard), the monitoring of the occupancy of a section of a building (e.g., for determining the load experienced by a section of a building in order to obtain the number of people in the section so as to control the heating, cooling, ventilation and lighting in accordance with the section occupancy for the purpose of saving energy, or to monitor building evacuation), and the monitoring of the vehicles on a road (e.g., for weighing the vehicles, particularly trucks, on a road for the purpose of road damage prevention, traffic monitoring, and truck axle counting).

Weighing systems in the prior art have involved conventional weighing scales (US 20150175365, US 20110238210) and load cells (IN 2014MU02525, US 20090292427, US 20160243610). A common type of weighing scale uses a spring and functions by balancing the weight due to gravity against the force on the spring. Another common type of weighing scale uses a balance beam, which functions by balancing the weight due to the mass of an object being weighed against the weight of a known mass. Load cells (e.g., hydraulic load cells, pneumatic load cells and strain gauges) are transducers that give an electrical signal that is proportional to the weight being measured. The weighing scales and load cells are limited in the weight range (particularly in the high end of the range), ruggedness, and applicability to the weighing of objects of large volume (such as the load experienced by a section of a building).

Self-sensing refers to the ability of a structural material to sense its own condition without the need for embedded or attached sensors. In other words, a self-sensing structural material is multifunctional material that is capable of both structural and sensing functions. Such a material is also said to be intrinsically smart.

Relevant attributes to be sensed include stress (which relates to the force), strain (which relates to the dimensional change), damage, temperature, etc. Stress and strain are linearly related to one another in the regime of elastic deformation. The self-sensing in cement-based materials is useful for the monitoring of bridges, highways, nuclear reactors, underground spaces, oil and gas wells that involve cementing, and deep sub-surface storage of natural gas or carbon dioxide. The sensing is preferably fast enough (short enough in the response time) that it is suitable for real-time monitoring.

Stress sensing relates to force sensing, which is pertinent to load monitoring and weighing. HVAC is the abbreviation for heating, ventilation, and air conditioning. It is directed at providing both thermal comfort and adequate indoor air quality. Weighing is needed for the monitoring of the HVAC-zone occupancy in buildings, so as to control the heating, cooling, ventilation and lighting of each HVAC zone of a building in accordance with the zone occupancy for the purpose of saving energy. Weighing is also useful for building evacuation monitoring. Weighing in highways and bridges is also needed for traffic control, the determination of the number of axles of a truck, the protection of highways and bridges from damage by overweight trucks, and city evacuation monitoring.

Strain monitoring is pertinent to operation control. Since dynamic strain occurs due to vibrations, strain monitoring is pertinent to structural vibration control. In normal structural operation, the strain is completely reversible and is in the elastic deformation regime. When the strain exceeds this regime, the strain is at least partly irreversible. The irreversibility means a permanent change in dimension. A permanent dimensional change is usually undesirable to the operation of a structure.

Damage monitoring relates to structural health monitoring and hazard mitigation. Damage tends to degrade the mechanical properties of a material. The mechanical properties are critical to the performance of a structural material. Therefore, damage is undesirable and can be hazardous. As a result, the ability to sense the damage is needed in order to assess the damage and consider repair. Due to the aging of the civil infrastructure, structural health monitoring is critically needed.

A change in temperature can affect structural operation. Excessively high temperatures can be due to a malfunction and can be hazardous. Thus, temperature monitoring is desirable for operation control and hazard mitigation.

The sensing of stress or strain is typically more subtle and more challenging than that of damage. In particular, the sensing of stress or strain in the elastic deformation regime is more challenging than the sensing of stress or strain in the regime that occurs when the elastic limit is exceeded. The deformation regime beyond the elastic limit is commonly known as plastic deformation. The high challenge of sensing stress or strain in the elastic deformation regime is because the strain and stress in this regime are typically small compared to those in the regimes beyond the elastic deformation regime. The regimes beyond the elastic deformation regime include the plastic deformation regime and the fracture regime. In general, the sensing of a small strain or stress is more challenging than that of a large strain or stress.

Sensing by numerous methods in the prior art is not effective for sensing strains in a cement-based material (particularly strains in the elastic deformation regime), though they may be effective for sensing damage, corrosion extent and/or ion concentration (e.g., chloride ion concentration) in a cement-based material. Examples of these methods include electrical resistivity measurement (WO 2015150463), piezoelectric sensing (US 20160266086), acoustic sensing (US 20150338380, US 20130036821), impedance measurement (US 20160054247), corrosion potential measurement (US 20130106447), radio wave sensing (U.S. Pat. No. 9,394,784), electromagnetic wave sensing (WO 2016019247), gamma radiation sensing (WO 2017030579), and fiber optic sensors (WO 2015118333). Sensing techniques that are amenable to the sensing of both elastic strain and damage are needed in order to provide information on the effects of the full range of mechanical deformation.

The strain in the elastic deformation regime is reversible, whereas the strain at fracture tends to be at least partly irreversible. As a result of the reversibility of the elastic strain upon unloading, the sensing of elastic strain requires a sensing output that is also reversible upon unloading. Otherwise, the sensing mechanism would work once only, i.e., being able to sense during the first encounter of strain or stress only. This requirement of reversibility adds to the challenge of sensing elastic strain or stress.

The attainment of sensing ability in a cement-based structure is most commonly achieved by embedding sensors in the structure. In other words, the cement-based material itself is not the sensor, i.e., it is not self-sensing. Examples of embedded sensors are fiber-optic sensors (WO 2015118333), piezoelectric sensors (US 20150338380), pressure sensors (US 20160201451), surface acoustic wave sensors (US 20130036821), temperature sensors (US 20150276702), microelectromechanical system sensors (US 20160266086), nuclear magnetic resonance sensors (WO 2015178883), radio frequency identification (RFID) tags (US 20140182848), integrated chips (WO 2016019247), and other sensors (US 20170160111, US 20170016874).

Compared to the use of attached or embedded sensors, the advantages of self-sensing include low cost, high durability, large sensing volume and absence of mechanical property loss. This is because structural materials are necessarily low in cost and high in durability. Attached sensors tend to be not durable, as they can be detached. Embedded sensors tend to degrade the mechanical properties of the structural material, in addition to be not amenable to repair or maintenance.

An admixture in a cement-based material refers to an ingredient other than cement, aggregates (e.g., fine aggregate in the form of sand and coarse aggregate in the form of gravel) and water that is included in the cement mix used to form the cement-based material. Examples of admixtures include polymer particles (e.g., latex particles), ceramic particles (e.g., silica particles), carbon particles (e.g., carbon black), and short fibers (e.g., short carbon fibers). Admixtures tend to be expensive compared to cement, aggregates or water.

Self-sensing has been reported in cement-based materials that have been rendered electrically conductive by the use of electrically conductive admixtures, such as carbon fibers (U.S. Pat. No. 5,817,944, WO 2017011460). The presence of a solid admixture in the cement mix tends to increase the viscosity of the slurry, thereby decreasing the workability of the slurry. The workability of the slurry is important for the fabrication of cement-based structures with various shapes and dimensions. In addition, the presence of a solid admixture tends to increase the air void content in the resulting cured cement-based material, due to the small air voids at the interface between the admixture and cement. An increase in air void content degrades the mechanical properties of the cement-based material. Furthermore, the admixtures are expensive, thus greatly increasing the cost of the cement-based material.

Self-sensing has also been reported in cement-based materials containing aggregate that has been coated with a polymer-based film containing carbon nanotubes (US 20160340245). The presence of the carbon nanotubes decreases the electrical resistivity of the cement-based material, but also decreases the elastic modulus (US 20160340245). The decreased modulus is partly because the bonding of the aggregate to the cement is degraded by the presence of the polymer-based film on the surface of the aggregate. In general, the bonding between polymer and cement is not adequate. This bonding is very important for the mechanical properties of the resulting cement-based material. Without adequate mechanical properties, a cement-based material is not useful as a structural material. Furthermore, the presence of carbon nanotubes increases the cost of the cement-based material significantly.

The electrical conductivity of a cement-based material enables the electrical resistivity (which is the reciprocal of the electrical conductivity) of the material to change with the condition of the material, thereby enabling the electrical resistance to indicate the condition. The phenomenon of the electrical resistivity of a material changing with strain is known as piezoresistivity, which must be distinguished from piezoelectricity. The piezoelectric effect involves energy conversion, but the piezoresistive effect does not.

Without the electrically conductive additive (whether the additive is an admixture or a coating on the aggregate), the cement-based material tends to be too high in the electrical resistivity for the resistance of a large volume of a cement-based structure to the effectively measured. In general, the measurement of a very high resistance is difficult, due to the need for a high voltage in order for an adequate electric current to flow in the material. Sources of high voltage are expensive and high voltage tends to be hazardous.

In the absence of a conductive additive, the electrical conduction of a cement-based material is dominated by ionic conduction rather than electronic conduction. The ionic conduction (and thereby the conductivity) is enhanced by the presence of moisture, chloride ions or other ionic species. The variability of the electrical resistivity with such chemical species makes the resistance change due to the condition (such as stress, strain, damage and temperature) not sufficiently clear or reproducible. However, in the presence of a conductive additive, the conduction is substantially electronic, such that the contribution of ionic conduction to the overall conduction is much reduced. As a result, in the presence of a conductive additive, the ability to sense a condition (such as stress, strain, damage and temperature) is less affected by the chemical species in the environment. On the other hand, in the absence of a conductive additive, the resistance can be used to indicate the concentration of chemical species in the form of ions in the cement-based material, due to the promotion of the ionic conduction by these ions (WO 2015150463).

Even in the absence of conductivity-enhancing chemical species in the environment, the electrical resistivity of a cement-based material without a conductive additive does not vary with the condition (such as stress, strain, damage and temperature) with adequate intensity or repeatability. This is due to the predominantly ionic nature of the conduction and the inadequate sensitivity of this conductivity to the condition.

Due to the abovementioned multiple reasons, the presence of a conductive additive is important for rendering a cement-based material to be able to sense its own condition effectively through the measurement of its electrical resistance. However, the conductive additive (whether particles, fibers or nanotubes) is very expensive compared to cement and the aggregate that is commonly used in concrete. Moreover, existing concrete structures rarely have any conductive additive in the concrete. As a consequence, the method of achieving self-sensing using conductive additives is not applicable to the vast majority (essentially all) of existing concrete structures.

The implementation of the resistance-based self-sensing involves the application of electrical contacts. The electrical resistance associated with an electrical contact must be small enough, so that it does not overshadow the resistance associated with the volume of the cement-based material. Thus, the electrical contacts must be high in quality, with the electrically conductive material (typically a metal) that makes up the electrical contact being in intimate contact with the cement-based material. Even if the resistance of the electrical contact is small, it may still vary as the condition (e.g., stress, strain, damage, temperature, etc.) changes. This means that both the resistance of the electrical contact and the resistance of the volume of the cement-based material change with the condition. The volume resistance is the quantity that is indicative of the condition being sensed. The variation of the contact resistance with the condition may cause the measured resistance (which includes both the contact resistance and the volume resistance) to be not indicative of the condition, thereby causing the sensing to be misleading. To alleviate this problem, four electrical contacts are used, with the outer two contacts for passing current and the inner two contacts for measuring the voltage. The resistance measured is this voltage divided by this current, and is the resistance between the two inner contacts. Because essentially no current flows through a voltage contact, there is essentially no potential (voltage) drop at each of the two voltage contacts. Therefore, the resistance obtained using four electrical contacts largely eliminates the contact resistance from the measured resistance. In contrast, the use of only two electrical contacts, with each contact serving for both current passing and voltage measurement, causes the measured resistance to include the contact resistance. In spite of the superior reliability of the method involving four electrical contacts compared to the method involving two electrical contacts, the former makes the implementation of the technique more difficult. In other words, installing four electrical contacts to measure the resistance of a segment of a cement-based structure is much more inconvenient (more labor intensive) than installing two electrical contacts.

The method of embedding two electrodes in a cement-based material for electrical measurement has been taught (EP 2947456). The two electrodes are metals that can be the same in composition or different in composition. An electrode can be in the form of a relatively inert metal such as titanium. It can also be in the form of a steel component (such as a steel reinforcement) that is commonly present in a cement-based structure anyway. The drawback of using two electrical contacts has been discussed above.

The alternating current (AC) impedance differs from the direct current (DC) resistance in that it is a complex quantity that consists of a real part (the resistance) and an imaginary part (the capacitance and inductance, with the capacitance being more relevant to the subject of this disclosure than the inductance).

The impedance depends on the AC frequency. The variation of the impedance with the frequency can be analyzed in terms of equivalent circuit models for describing the electrical behavior. The analysis typically involves the fitting of the curve in the Nyquist plot (plot of the imaginary part of the impedance to the real part of the impedance for various frequencies). However, the equivalent circuit model obtained by the curve fitting is not unique. As a consequence of the non-uniqueness, the values of the circuit parameters (resistances and capacitances) in the circuit model are only meaningful in the context of the particular circuit model and are not generally meaningful.

Because the impedance includes the resistance as its real part, the measurement of the impedance involves the same issues as mentioned above in relation to the measurement of the resistance. An issue pertains to the abovementioned requirement that the electrical contacts are associated with low values of the contact resistance. Another issue pertains to the abovementioned need for using four electrical contacts rather than two electrical contacts.

The measurement of the capacitance has its issues too. An issue pertains to the fact that the impedance meter (often called an LCR meter) is not designed for measuring the capacitance of an electrical conductor. When an impedance meter is used for testing a conductive material, the capacitance value that it outputs can be off from the true value by a large amount (even off by orders of magnitude). Depending on the composition and ion concentration, a cement-based material can be conductive enough for this issue to be pertinent.

The parallel-plate capacitor geometry is commonly and classically used for measuring the capacitance of a material that is sandwiched by the two facing plates (i.e., two conductor plates commonly referred to as electrodes). The capacitance is in the direction perpendicular to the plates. Due to the small thickness of the material being tested between the two plates and the large area, the capacitance can be rather large. Thus, this variation of the parallel-plate capacitor geometry is effective for obtaining information that pertains to the capacitance. On the other hand, due to the small thickness and large area, the resistance can be rather small, though the value depends on the resistivity of the material.

In a less common variation of the parallel-plate capacitor geometry, the material being tested is positioned between the parallel proximate edge surfaces of two coplanar plates (EP 3115781). In other words, the material is sandwiched by these edge surfaces, so that the thickness of the sandwich is large and the area of the sandwich is small. The capacitance measured is in the direction perpendicular to the two edge surfaces. This geometry tends to be associated with a small capacitance, due to the large thickness of the material being tested between the two edges and the small area of the capacitor. Thus, this variation of the parallel-plate capacitor geometry is not effective for obtaining information that pertains to the capacitance. On the other hand, due to the large thickness and small area, the resistance tends to be rather large, though this value depends on the resistivity of the material.

A parallel-plate capacitor actually involves three capacitors in series electrically, whether the electrodes are facing or coplanar. The three capacitors that are electrically in series consist of the capacitance of the sandwiched volume of the material being tested, and the capacitance of each of the two interfaces, with each interface being that between the sandwiched material and one of the two electrodes. The well-known equation for capacitors in series is $$1/C = 1/C_1 + 1/C_2 + 1/C_3, \qquad (1)$$

where C is the overall capacitance of the three capacitors (with capacitances $C_1$, $C_2$ and $C_3$) in series. Hence, the measured capacitance C of the parallel-plate capacitor is given by $$1/C = 1/C_v + 2/C_i, \qquad (2)$$

where $C_v$ is the capacitance of the volume of sandwiched material and $C_i$ is the capacitance of one of the two interfaces. Thus, neglecting thereby assuming that $C=C_v$, can result in an incorrect determination of $C_v$ from the measured C.

The relative electric permittivity is a material property that reflects the degree of damage or the ion concentration in the material. For example, the permittivity of a cement-based material increases with the chloride ion concentration in the material, thereby allowing the permittivity to indicate the chloride ion concentration (EP 3115781).

The relative permittivity κ is obtained from $C_v$ using the well-known equation $$C_v = \varepsilon_o \kappa A/l, \quad (3)$$

where $\varepsilon_o$ is the permittivity of free space ($8.85 \times 10^{-12}$ F/m), A is the area of the sandwich (i.e., the area of each electrode, which is the same as the area of the sandwiched material being tested), and l is the thickness of the material sandwiched by the two electrodes. Without a reliable determination of $C_v$, κ cannot be reliably obtained by using Eq. (3). Specifically, neglecting the term $2/C_i$ in Eq. (2) causes $1/C_v$ to be overestimated, thus causing $C_v$ to be underestimated, and causing κ to be also underestimated.

Capacitive sensing is important for touch sensing, as needed for touch screens, which are commonly used in electronic devices such as computers. Touch sensing is based on the concept that the human finger is an electrical conductor and its contact with an electrical circuit changes the capacitance of the circuit. In connection with touch screens, a large variety of electrode patterns and associated circuits have been taught (US 20170269779, US 20170024033). However, such sensing systems are not capable of and not applicable to the sensing of the force exerted on a cement-based structure. The use of such concepts for the sensing of the force exerted on a cement-based structure would be very expensive, due to the electrical circuit. In addition, the durability of the circuit under substantial mechanical force is low.

The embedment of electrodes in a wet cement-based material (i.e., cement-based material that is either only partly hydrated or not yet hydrated) for measuring the electrical impedance of the wet material as a function of the frequency has been taught for the purpose of obtaining information on the physical properties of the wet material (US 20160054247). Due to the high ionic conductivity resulting from the water in the wet material, the conductivity or impedance of the wet material is very different from that of the dry (hydrated) material. Although the knowledge of the physical properties of the wet material is useful for understanding the basic science of the wet material, the teaching is not directed at sensing the condition of the dry (hydrated) material. The hydrated (dry) state is the state in which cement-based structures are used, so it is practically more important than the wet state, which is important only for the process of installation of a cement-based slurry in a structure.

The measurement of the interaction of gamma radiation (which is high-energy electromagnetic radiation) of various frequencies with a cement-based structure can provide information that reflects the condition of the structure (WO 2017030579, WO 2016148696). However, this method requires a gamma radiation source and instrumentation for detecting and analyzing the interaction of the gamma ray with the cement-based structure. Both the source and the instrumentation are expensive. In addition, the gamma radiation (even more energetic than X-ray) is hazardous.

Piezoelectric cement-based materials are commonly obtained by incorporating a piezoelectric material (commonly in the form of ceramic particles such as lead zirconotitanate, which is abbreviated PZT) in the cement-based material. The incorporation is aimed only at damage sensing (WO 2008094358), salt corrosion resistance enhancement (US 20080179993), and vibration reduction (US 20110252734, US 20110252715).

The direct piezoelectric effect converts mechanical energy to electrical energy. Thus, in response to mechanical energy input, electrical energy output occurs. The electrical energy output manifests itself as the generation of voltage and/or current. Hence, this effect can be used for the sensing of the mechanical energy input through measurement of the electrical energy output. For a static force input, the output is a static open-circuit voltage or a pulse of a close-circuit current. The static open-circuit voltage can be measured using a voltmeter. However, due to its short duration, the current pulse requires for its measurement an instrument that is capable of rapid real-time response. An example of such an instrument is an oscilloscope, which is a type of electronic test instrument that provides plots of constantly varying signal voltages as a function of time. As a result, the measurement of a current pulse is relatively demanding in the instrumentation. For a dynamic force input, the electrical output is dynamic for both voltage and current, as can be measured by using an oscilloscope. Therefore, the measurement of the dynamic electrical output is relatively demanding in the instrumentation.

The measurement of the impedance or capacitance requires an impedance meter (LCR meter). The higher the frequency, the more expensive is the meter, and the less effective is the sensing of chemical species that cannot respond to rapid changes in the polarity of the AC electric field used for the impedance or capacitance measurement. Examples of such chemical species are ionic species (e.g., chloride ions) and molecular species. Cement-based materials contain ions, notably calcium ions. Chloride ions are undesirable in cement due to their promotion of the corrosion of the steel reinforcement that is commonly present in a cement-based material. Thus, the effectiveness of a technique that operates at a low frequency is desirable. Relatively high frequencies of 16 kHz (1 kHz=1000 Hz) or above are used in prior work (EP 3115781).

The present invention is directed at overcoming these and other deficiencies in the art.

SUMMARY OF THE INVENTION

This invention provides a cement-based material system for the self-sensing of the force exerted on the cement-based material. It also provides a cement-based material system for weighing. This force is selected from the group consisting of: compressive force, tensile force, flexural force, shear force, torsional force, and combinations thereof. In addition, this invention provides a method for the self-sensing of the force exerted on a cement-based material.

The measurement involves using two electrodes on the same surface of the cement-based material. The force to be sensed is exerted on the cement-based material, particularly on the part of the cement-based material surface between the two electrodes. The capacitance measured between the two electrodes serves as an indicator of the force or weight.

No particular admixture is required for the abovementioned cement-based material. This is unexpected and allows the disclosed technique to be broadly applied to existing structures, which rarely contain particular admixtures. This means that the technique is applicable to both new and existing structures.

The effectiveness of the disclosed technique for sensing small forces is unexpectedly high. This capability allows the sensing of small forces such as the weight of individual persons—even that of individual children. The minimum stress (normal force per unit area) that can be detected is 0.3 kPa. The sensing of large forces (such as the weight of cars and trucks) is also effective.

This disclosure describes embodiments of the cement-based material systems for self-sensing and weighing, and embodiments of the method of the self-sensing of the force exerted on a cement-based material.

BRIEF DESCRIPTION OF THE DRAWINGS

FIG. 4 illustrates the testing configurations used in Examples 1-3 that pertain to the low-stress regime. The specimen size is nominally 150 mm×150 mm×10 mm (actual size 149.12 mm×146.5 mm×10.45 mm). A dielectric film (three layers of double-sided adhesive tape) is positioned between each aluminum electrode and the specimen. Two electrodes are applied to each of the top and bottom surfaces. A normal force is applied to the entirety of the honeycomb-shaded area (30 mm wide) between the electrodes. All dimensions are in mm. The vertical dimensions are not to scale.

FIG. 5 shows the effect of dynamic uniaxial compression on the capacitance, as investigated using configuration I in the low-stress regime (FIGS. 4(a) and 4(b)). The stress ranges from 300 to 1500 Pa.

FIG. 6 shows the variation of the capacitance with the compressive stress, as obtained using configuration I in the low-stress regime (FIGS. 4(a) and 4(b)). The stress ranges from 300 to 1500 Pa.

FIG. 7 shows the variation of the capacitance with the flexural (bending) stress, as obtained using configuration II in the low-stress regime (FIGS. 4(a) and 4(c)). The stress ranges from 300 to 1500 Pa.

FIG. 8 shows the effect of dynamic uniaxial compression on the capacitance, as investigated using configuration I in the low-stress regime (FIGS. 4(a) and 4(b)). The stress ranges from 900 Pa to 4500 Pa.

FIG. 9 shows the effect of dynamic flexure on the capacitance, as investigated using configuration II (FIGS. 4(a) and 4(c)) in the low-stress regime. The flexural stress ranges from 900 Pa to 4500 Pa. A flexural stress of 4000 Pa corresponds to a normal stress of 75.2 Pa.

FIG. 11 shows the effect of dynamic flexure on the capacitance, as investigated using configuration II (FIGS. 4(a) and 4(c)) in the low-stress regime up to about 7400 Pa in the flexural stress, i.e., up to about 139 Pa in the normal stress. A flexural stress of 4000 Pa corresponds to a normal stress of 75.2 Pa.

FIG. 12 illustrates the testing configurations used in Examples 4-8, which pertain to the medium-stress regime (about 4-19 kPa in the normal stress) and high-stress regime (above about 19 kPa in the normal stress). As shown in FIGS. 12(a) and 12(b), a dielectric film (one layer of double-sided adhesive tape) is positioned between each aluminum electrode and the specimen. The vertical dimensions in FIGS. 12(a) and 12(b) are not to scale. All dimensions are in mm.

FIG. 13 shows the results for configuration III (FIG. 12(a)) in the medium-stress and high-stress regimes. It shows the effect of the applied normal compressive loading at progressively increasing normal stress amplitude above 3.4 kPa. The dashed curve gives the normal compressive stress; the solid curve gives the capacitance in FIG. 13(a) and FIG. 13(c) and gives the fractional decrease in capacitance in FIG. 13(b) and FIG. 13(d).

FIG. 14 shows the results for configuration III (FIG. 12(a)) in the medium-stress regime (about 4-19 kPa in the normal stress) and high-stress regime (above about 19 kPa in the normal stress). It shows the effect of the applied normal compressive stress (above 3.4 kPa) on the capacitance. The solid curve (■) is obtained during loading; the dashed curve (Δ) is obtained during unloading.

FIG. 15 shows the results for configuration IV (FIG. 12(b)) in the medium-stress regime (about 4-19 kPa in the normal stress) and high-stress regime (above about 19 kPa in the normal stress). It shows the effect of the applied normal stress during flexure at progressively increasing normal stress amplitude above 3.4 kPa. The dashed curve gives the normal stress; the solid curve gives the capacitance in FIG. 15(a) and FIG. 15(c) and gives the fractional decrease in capacitance in FIG. 15(b) and FIG. 15(d).

FIG. 16 shows the results for configuration IV (FIG. 12(b)) in the medium-stress regime (about 4-19 kPa in the normal stress) and high-stress regime (above about 19 kPa in the normal stress). It shows the effect of the applied normal stress during flexure on the capacitance. The solid curve (■) is obtained during loading; the dashed curve (Δ) is obtained during unloading.

DETAILED DESCRIPTION OF THE INVENTION

Figure 1:
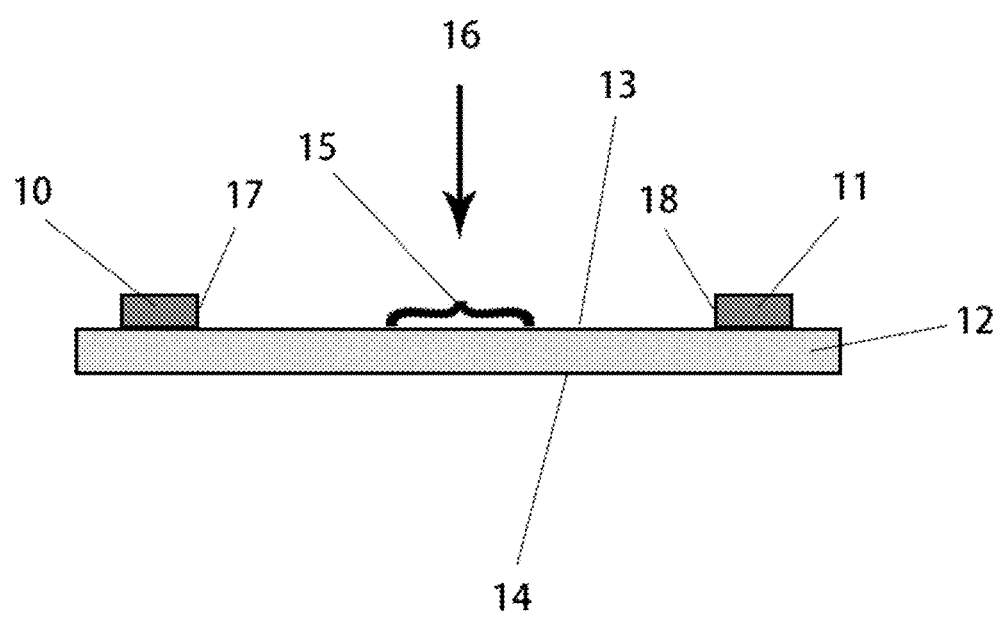
FIG. 1 shows the side view of a basic cement-based material system for the self-sensing of the force (16) exerted on surface 13 of the cement-based material (12). This configuration involves two electrodes (10 and 11) positioned on surface 13. The proximate edges (17 and 18) of the two electrodes (10 and 11) are essentially parallel. The area of force application (15) is located in the region that extends from edge 17 to edge 18.
Figure 2:
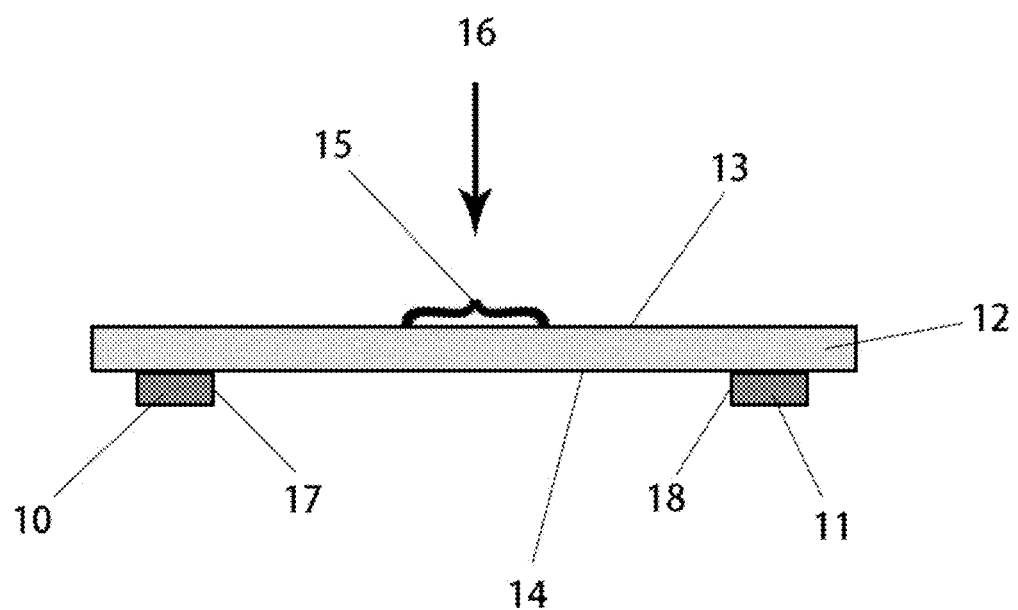
FIG. 2 shows the side view of another basic cement-based material system for the self-sensing of the force (16) exerted on surface 13 of the cement-based material (12). This configuration involves two electrodes (10 and 11) positioned on surface 14, which is essentially opposite to surface 13. The proximate edges (17 and 18) of the two electrodes (10 and 11) are essentially parallel. The area of force application (15) is located in the region on surface 13 that extends from edge 17 to edge 18.
Figure 3:
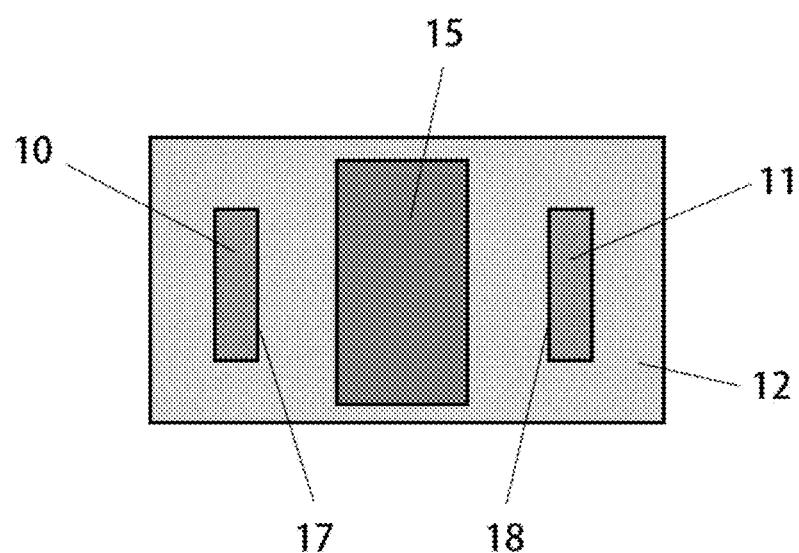
FIG. 3 shows the top view of the basic cement-based material system for the self-sensing of the force (16) exerted on surface 13 of the cement-based material (12). This top view corresponds to the side view shown in FIG. 1. The area of force application (15) extends along the length of the electrodes, such that its length can exceed the length of the electrodes. The top view corresponding to FIG. 2 is the same as FIG. 3, except that the electrodes (10 and 11) are on surface 14 and are thus not visible from the top.

This invention provides a cement-based material system for the self-sensing of the force exerted on the cement-based material. This force is selected from the group consisting of: compressive force, tensile force, flexural force, shear force, torsional force, and combinations thereof.

This system for the self-sensing of the force exerted on the cement-based material comprises electrode A and electrode B, which are electrically conductive. The system also comprises the cement-based material, which exhibits exterior geometric surface, which is selected from the group consisting of surface I, surface II, and combinations thereof. Surface I is the surface on which the force is exerted, and surface II is the surface essentially opposite to surface I. Electrodes A and B are positioned on surface S, which is selected from the group consisting of surface I and surface II. The proximate edges of the electrodes A and B are essentially parallel. The edges are separate from one another by a distance.

In the cement-based material system for the self-sensing of the force exerted on the cement-based material, the force is exerted on a part of surface I. The part is positioned in a region, which extends along a line that is essentially perpendicular to the edges, that extends from the location of one edge to the location of the other edge, and that is essentially in the plane of surface I. The part also extends along the length of the electrodes. The length of an electrode is in a direction essentially parallel to the edge of the electrode. The length of the part in the direction essentially parallel to the length of the electrodes can exceed the length of the electrodes, although it can be shorter than the electrodes. That the part can be longer than the electrodes is because of the spreading of the electric field lines away from the ends of the length of the electrodes, so that the electric field emanating from the electrodes reaches locations beyond the ends of the length of the electrodes.

In the cement-based material system for the self-sensing of the force exerted on the cement-based material, the area of electrode A is substantially smaller than the area of the surface; the area of electrode B is also substantially smaller than the area of the surface; the dimensions of electrode A and the dimensions of electrode B are essentially equal; the geometric shape of electrode A and the geometric shape of electrode B are essentially the same; the composition of electrode A and the composition of electrode B are essentially the same; electrode A and electrode B are electrically oppositely charged. That electrodes A and B are electrically oppositely charged results from an applied alternating electric current, which flows from electrode A to electrode B and flows in the cement-based material. Electrode A and electrode B exhibit capacitance between them. This capacitance comprises the capacitance of the cement-based material. The capacitance ranges from 0.1 pF (1 pF=$10^{-12}$ F) to 1 μF (1 μF=$10^{-6}$ F), and exhibits direction, which is essentially parallel to surface S and essentially perpendicular to the proximate edges. The capacitance serves as an indicator of the force.

In the cement-based material system for the self-sensing of the force exerted on the cement-based material, the force is preferably essentially perpendicular to surface I. The force can result in a compressive stress in the direction of the force, a flexural (bending) stress in a direction perpendicular to the force, or other types of stress. Essentially uniaxial compressive stress occurs if the cement-based material is essentially fully supported throughout the area of force application. Flexural (bending) stress occurs if the cement-based material is supported only at locations away from the area of force application.

In the cement-based material system for the self-sensing of the force exerted on the cement-based material, the distance preferably ranges from 1 mm to 1 m.

In the cement-based material system for the self-sensing of the force exerted on the cement-based material, the frequency of the applied alternating electric current preferably ranges from 1 Hz to 100 kHz.

The cement-based material system for the self-sensing of the force exerted on the cement-based material preferably also comprises dielectric films A and B. The dielectric film A is positioned between electrode A and surface S; the dielectric film B is positioned between electrode B and surface S. The dielectric film A is in contact with the entire area of the electrode A; the dielectric film B is in contact with the entire area of the electrode B. The dielectric films A and B are in contact with surface S.

The cement-based material system for the self-sensing of the force exerted on the cement-based material preferably also comprises dielectric films A and B. The dielectric film A is positioned between electrode A and surface S; the dielectric film B is positioned between electrode B and surface S. The dielectric film A is in contact with the entire area of electrode A; the dielectric film B is in contact with the entire area of electrode B. The dielectric films A and B are in contact with surface S. The dielectric film A has thickness preferably less than 200 μm; the dielectric film B has thickness preferably less than 200 μm. The thickness of the dielectric film A and the thickness of the dielectric film B are essentially equal.

In the cement-based material system for the self-sensing of the force exerted on the cement-based material, electrode A preferably comprises a plurality of parallel strips A and electrode B preferably comprises a plurality of parallel strips B. All of parallel strips A are electrically connected; all of parallel strips B are electrically connected. The number of strips in parallel strips A and the number of strips in parallel strips B are essentially equal. Parallel strips A and parallel strips B are interdigitated. The interdigitated configuration is akin to two combs that have their parallel strips interposed and positioned together. It is also akin to two hands that have their fingers interposed and positioned together.

In the cement-based material system for the self-sensing of the force exerted on the cement-based material, both electrode A and electrode B preferably comprise material selected from the group consisting of: metal, metal alloy, metal-based material, metal-matrix composite, aluminum, copper, nickel, titanium, steel, electrically conductive polymer, and combinations thereof.

The cement-based material system for the self-sensing of the force exerted on the cement-based material preferably also comprises dielectric film A, and dielectric film B. Dielectric film A is positioned between electrode A and surface S, and dielectric film B is positioned between electrode B and surface S. Dielectric film A is in contact with the entire area of electrode A; dielectric film B is in contact with the entire area of electrode B. Dielectric films A and B are in contact with surface S. Dielectric film A is bonded to electrode A; dielectric film B is bonded to electrode B. The dielectric films A and B are bonded to surface S. An example of bonding is adhesive bonding.

The cement-based material system for the self-sensing of the force exerted on the cement-based material preferably also comprises dielectric film A, and dielectric film B. The dielectric film A is positioned between electrode A and surface S, the dielectric film B is positioned between electrode B and surface S. Dielectric film A is in contact with the entire area of electrode A; dielectric film B is in contact with the entire area of electrode B. The dielectric films A and B are in contact with the surface S. Dielectric film A is fastened to electrode A; dielectric film B is fastened to electrode B. Dielectric films A and B are fastened to surface S. An example of fastening is clamping.

This invention also provides a cement-based material system for weighing, i.e., for determining weight. The weight is applied to the cement-based material. The system comprises electrode A and electrode B, which are both electrically conductive. The system also comprises the cement-based material, which exhibits exterior geometric surface. The exterior geometric surface is selected from the group consisting of surface I, surface II, and combinations thereof. Surface I is the surface to which the weight is applied. Surface II is the surface essentially opposite to surface I. Electrode A and electrode B are positioned on surface S, which is selected from the group consisting of: surface I, and surface II. The proximate edges of electrode A and electrode B are essentially parallel. The edges are separate from one another by a distance. The weight is applied to a part of said surface I. The part is positioned in a region, which extends along a line that is essentially perpendicular to the edges, that extends from the location of one edge to the location of the other edge, and that is essentially in the plane of surface I. Electrode A is substantially smaller in area than surface S; electrode B is also substantially smaller in area than surface S. Electrode A and electrode B are essentially the same in dimensions; they are essentially the same in geometric shape; they are essentially the same in composition; they are electrically oppositely charged. That electrodes A and B are electrically oppositely charged results from an applied alternating electric current, which flows from electrode A to electrode B, and flows in the cement-based material. Electrode A and electrode B exhibit capacitance between them. This capacitance comprises the capacitance of the cement-based material. The capacitance ranges from 0.1 pF to 1 µF, and exhibits direction, which is essentially parallel to surface S and essentially perpendicular to the proximate edges. The capacitance serves as an indicator of the weight.

In the cement-based material system for weighing, the distance preferably ranges from 1 mm to 1 m.

In the cement-based material system for weighing, the frequency of the applied alternating electric current is preferably ranges from 1 Hz to 100 kHz.

The cement-based material system for weighing preferably also comprises dielectric films A and B. The dielectric film A is positioned between electrode A and surface S; the dielectric film B is positioned between electrode B and surface S. The dielectric film A is in contact with the entire area of the electrode A; the dielectric film B is in contact with the entire area of the electrode B. The dielectric films A and B are in contact with surface S.

The cement-based material system for weighing preferably also comprises dielectric films A and B. The dielectric film A is positioned between electrode A and surface S; the dielectric film B is positioned between electrode B and surface S. The dielectric film A is in contact with the entire area of electrode A; the dielectric film B is in contact with the entire area of electrode B. The dielectric films A and B are in contact with surface S. The dielectric film A has thickness preferably less than 200 µm; the dielectric film B has thickness preferably less than 200 µm. The thickness of the dielectric film A and the thickness of the dielectric film B are essentially equal.

In the cement-based material system for weighing, electrode A preferably comprises a plurality of parallel strips A and electrode B preferably comprises a plurality of parallel strips B. All of parallel strips A are electrically connected; all of parallel strips B are electrically connected. The number of strips in parallel strips A and the number of strips in parallel strips B are essentially equal. Parallel strips A and parallel strips B are interdigitated.

In the cement-based material system for weighing, both electrode A and electrode B preferably comprise material selected from the group consisting of: metal, metal alloy, metal-based material, metal-matrix composite, aluminum, copper, nickel, titanium, steel, electrically conductive polymer, and combinations thereof.

The cement-based material system for weighing preferably also comprises dielectric film A, and dielectric film B. Dielectric film A is positioned between electrode A and surface S, and dielectric film B is positioned between electrode B and surface S. Dielectric film A is in contact with the entire area of electrode A; dielectric film B is in contact with the entire area of electrode B. Dielectric films A and B are in contact with surface S. Dielectric film A is bonded to electrode A; dielectric film B is bonded to electrode B. The dielectric films A and B are bonded to surface S. An example of bonding is adhesive bonding.

The cement-based material system for weighing preferably also comprises dielectric film A, and dielectric film B. The dielectric film A is positioned between electrode A and surface S, the dielectric film B is positioned between electrode B and surface S. Dielectric film A is in contact with the entire area of electrode A; dielectric film B is in contact with the entire area of electrode B. The dielectric films A and B are in contact with the surface S. Dielectric film A is fastened to electrode A; dielectric film B is fastened to electrode B. Dielectric films A and B are fastened to surface S. An example of fastening is clamping.

This invention also provides a method of the self-sensing of the force exerted on a cement-based material, which exhibits exterior geometric surface. This force is selected from the group consisting of: compressive force, tensile force, flexural force, shear force, torsional force, and combinations thereof. The exterior surface is selected from the group comprising surface I, surface II, and combinations thereof. Surface I is the surface on which the force is exerted; surface II is the surface essentially opposite to surface I. The force is exerted on a part of surface I. The method comprises step (a) and step (b). Step (a) involves positioning electrode A and electrode B on surface S. Electrode A and electrode B are electrically conductive. Surface S is selected from the group consisting of surface I and surface II. The proximate edges of electrode A and electrode B are essentially parallel. The edges are separate from one another by a distance. The force is exerted on a part of surface I. This part is positioned in a region, which extends along a line that is essentially perpendicular to the edges, that extends from the location of one edge to the location of the other edge, and that is essentially in the plane of surface I. The area of electrode A is substantially smaller than the area of surface S; the area of electrode B is substantially smaller than the area of surface S; the dimensions of electrode A and the dimensions of electrode B are essentially equal; the geometric shape of electrode A and the geometric shape of electrode B are essentially the same; the composition of electrode A and the composition of electrode B are essentially the same. Step (b) involves measuring the capacitance between electrode A and electrode B. The capacitance ranges from 0.1 pF to 1 µF and serves as an indicator of the force.

Concerning the method, the force is preferably essentially perpendicular to the surface S.

Concerning the method, the distance preferably ranges from 1 mm to 1 m.

Concerning the method, the frequency of the capacitance preferably ranges from 1 Hz to 100 kHz.

The method preferably also comprises positioning dielectric film A between electrode A and the surface S, and preferably also comprises positioning dielectric film B between electrode B and the surface S. The dielectric film A is in contact with the entire area of the electrode A; the dielectric film B is in contact with the entire area of the electrode B. The dielectric films A and B are in contact with the surface S.

The method preferably also comprises positioning dielectric film A between electrode A and the surface S, and preferably also comprises positioning dielectric film B between electrode B and the surface S. The dielectric film A is in contact with the entire area of the electrode A; the dielectric film B is in contact with the entire area of the electrode B. The dielectric films A and B are in contact with the surface S. Each of the dielectric films A and B has thickness preferably less than 200 µm. The thickness of the dielectric film A and the thickness of the dielectric film B are essentially equal.

The method preferably also comprises positioning dielectric film A between electrode A and the surface S, and preferably also comprises positioning dielectric film B between electrode B and the surface S. The dielectric film A is in contact with the entire area of the electrode A; the dielectric film B is in contact with the entire area of the electrode B. The dielectric films A and B are in contact with the surface S. The dielectric film A is held to the electrode A by adhesion; the dielectric film B is held to the electrode B by adhesion. The dielectric films A and B are held to the surface S by adhesion. An example of bonding is adhesive bonding.

The method preferably also comprises positioning dielectric film A between electrode A and the surface S, and preferably also comprises positioning dielectric film B between electrode B and the surface S. The dielectric film A is in contact with the entire area of the electrode A; the dielectric film B is in contact with the entire area of the electrode B. The dielectric films A and B are in contact with the surface S. The dielectric film A is held to the electrode A by adhesion; the dielectric film B is held to the electrode B by fastening. The dielectric films A and B are held to the surface S by fastening. An example of fastening is clamping.

Concerning the method, the electrode A preferably comprises a plurality of parallel strips A, and the electrode B preferably comprises a plurality of parallel strips B. All of parallel strips A are electrically connected; all of parallel strips B are electrically connected. The number of strips in parallel strips A and the number of strips in parallel strips B are essentially equal. The parallel strips A and the parallel strips B are interdigitated.

Concerning the method, both electrode A and electrode B preferably comprise material selected from the group consisting of: metal, metal alloy, metal-based material, metal-matrix composite, aluminum, copper, nickel, titanium, steel, electrically conductive polymer, and combinations thereof.

EXAMPLES

Example 1

This Example pertains to the raw materials used in preparing the cement-based material used for testing a cement-based material system in terms of the effectiveness of the self-sensing of the force exerted on the cement-based material in the low-stress regime (below about 4 kPa=4000 Pa in the normal stress). A normal stress of 4000 Pa corresponds to a flexural (bending) stress of 213 kPa (1 kPa=1000 Pa).

Portland cement (Type I, ASTM C150, from Lafarge Corp., Southfield, Mich.) is used. The cement-based material studied is cement paste in solid (cured) form; no aggregate or admixture is used. The water/cement ratio is 0.35.

Cement powder and water are mixed for 5 min using a rotary mixer with a flat beater. The cement mix is poured to an oiled plastic mold. After filling the mold, an external vibrator is used to facilitate compaction and diminish the air bubbles. The specimens are demolded after 24 h and then cured at a relative humidity of nearly 100% for 28 days. The demolded specimens are ground and burnished to ensure that the surfaces are smooth before capacitance measurement. The cement-based material specimens are in the form of square slabs of size 149.12 mm×146.50 mm×10.45 mm.

Example 2

This Example pertains to a method of testing a cement-based material system for the effectiveness of the self-sensing of the force exerted on the cement-based material in the low-stress regime (below about 4 kPa in the normal stress). A normal stress of 4 kPa (4000 Pa) corresponds to a flexural (bending) stress of 213 kPa. The force is compressive for configuration I (FIGS. 4(a) and 4(b)) and flexural for configuration II (FIGS. 4(a) and 4(c)). These configurations are explained below.

For measuring the in-plane capacitance, two electrodes on the same surface of the cement specimen, with their proximate edges separated by a distance of 119.12 mm, are used (FIG. 4). Aluminum foil is used as the electrode. Three stacked layers of commercial double-sided adhesive tape (79 μm thick per layer) are positioned between the aluminum foil (146.5 mm×10.0 mm) and the specimen in order to adhere the specimen to the electrode. The tape also serves as a dielectric film, which is used due to the fact that an LCR meter is not designed for measuring the capacitance of a conductor. Although the cement-based material is not conductive enough to require the dielectric film, the film is used in order to ensure stability in the capacitance measurement.

Figure 4A:
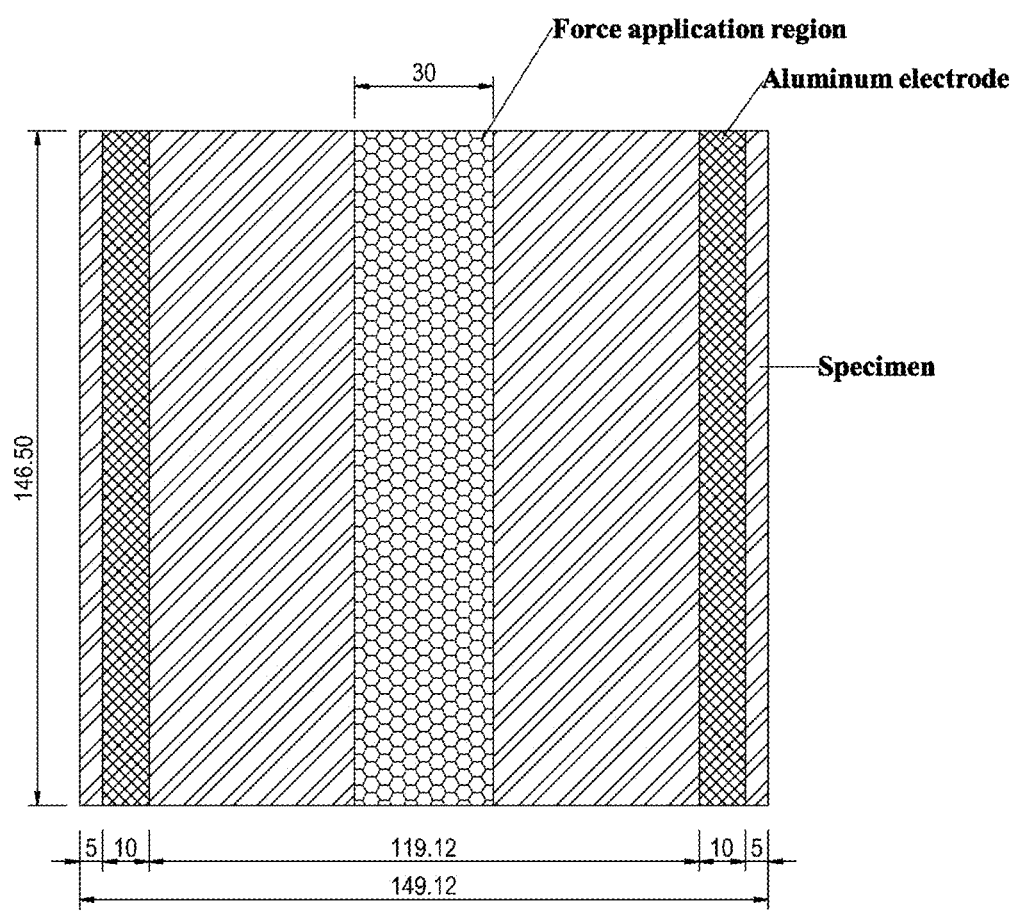
FIG. 4(a) shows the top view of testing configurations I and II.
Figure 4B:
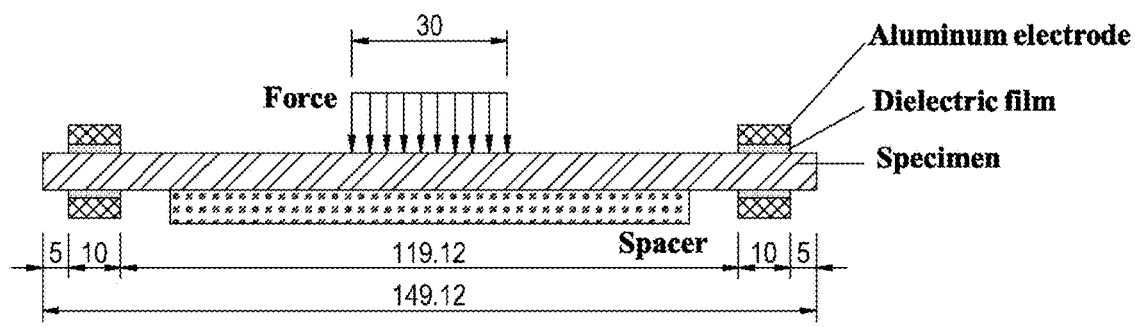
FIG. 4(b) shows the side view of testing configuration I, with a normal uniaxial compressive force applied. A spacer is positioned below the specimen over a region that includes the area of force application in order to ensure uniaxial compressive loading and to avoid the application of force on the bottom electrodes. The small compressive stress of 10.56 Pa corresponding to the pre-load applied is not counted in the data obtained using configuration I and presented in this document.
Figure 4C:
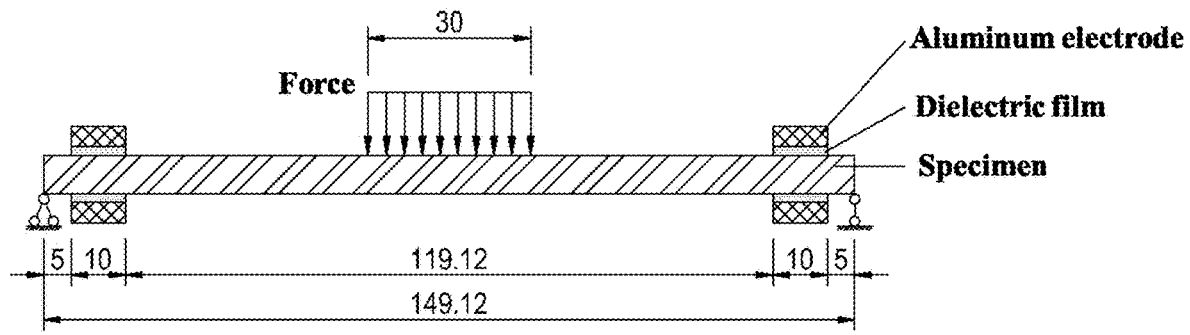
FIG. 4(c) shows the side view of testing configuration II, with two parallel supports along the entire lengths of two opposite edges of the specimen for providing flexure (three-point bending) and for avoiding the application of force on the bottom electrodes. The small flexural stress of 561.7 Pa corresponding to the pre-load applied is not counted in the data obtained using configuration II and presented in this document.

In the stress sensing investigation, force in the direction perpendicular to the plane of the specimen is applied to the 146.5 mm×30 mm region between the two electrodes (FIG. 4). The force is provided by using known weights positioned above this region. Two testing configurations are used. In configuration I (FIGS. 4(a) and 4(b)), the specimen is supported by using a spacer beneath the specimen, such that the spacer extends beyond the region of normal force application, so that the applied normal stress is purely compressive. In configuration II (FIGS. 4(a) and 4(c)), the specimen has two supports (146.5 mm×2.5 mm each) that are positioned along the entire lengths of the two opposite edges of the specimen, so that this configuration gives flexure under three-point bending.

The highest compressive stress is within the elastic regime of the specimen. The compressive modulus is 2.92 GPa and the compressive strength is 57.9 MPa.

The capacitance is measured between the two electrodes, using a precision RLC meter (Instek LCR-816 High Precision LCR Meter, 100 Hz-2 kHz). The frequency used is 2.000 kHz. The electric field is in the plane of the specimen and corresponds to a voltage of 0.500 V over the gap of 119.12 mm between the proximate edges of the two electrodes. The capacitance reported is for the equivalent electrical circuit of a capacitance and a resistance in parallel.

Example 3

This Example pertains to the results of testing a cement-based material system for the effectiveness of the self-sensing of the force exerted on the cement-based material in the low-stress regime (below about 4 kPa in the normal stress). A normal stress of 4 kPa corresponds to a flexural (bending) stress of 213 kPa. The force is compressive for configuration I (FIGS. 4(a) and 4(b)) and flexural for configuration II (FIGS. 4(a) and 4(c)).

Figure 5A:
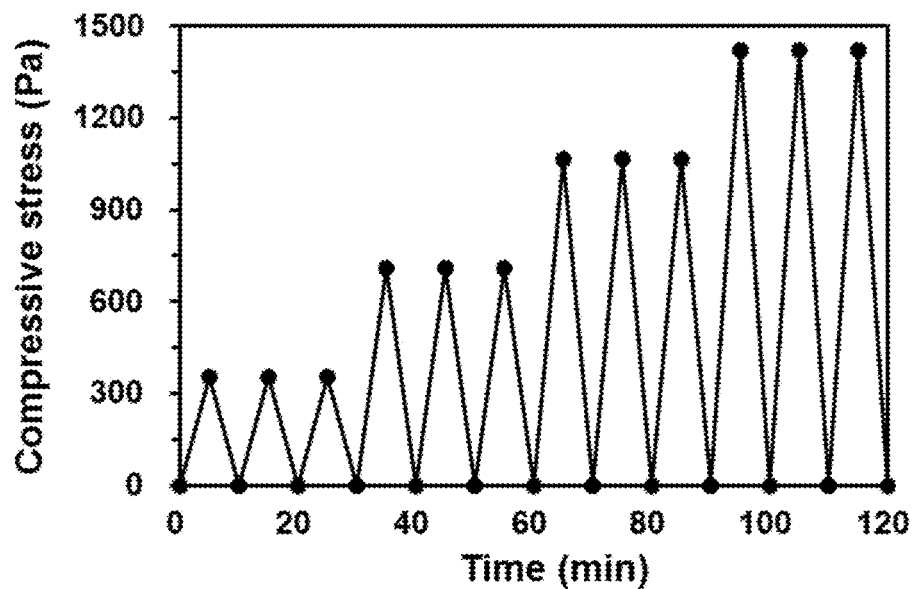
FIG. 5(a) shows the variation of the compressive stress with time. The stress amplitude is progressive increased, such that there are three cycles at each stress amplitude.
Figure 5B:
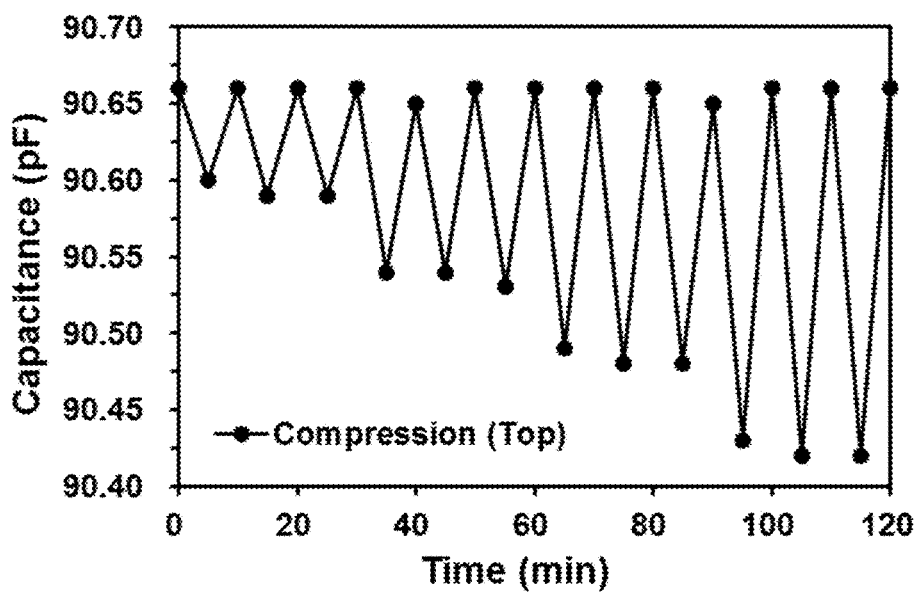
FIG. 5(b) shows the corresponding variation with time of the capacitance measured at the top surface. The capacitance decreases upon loading, such that the effect increases with increasing stress amplitude.
Figure 5C:
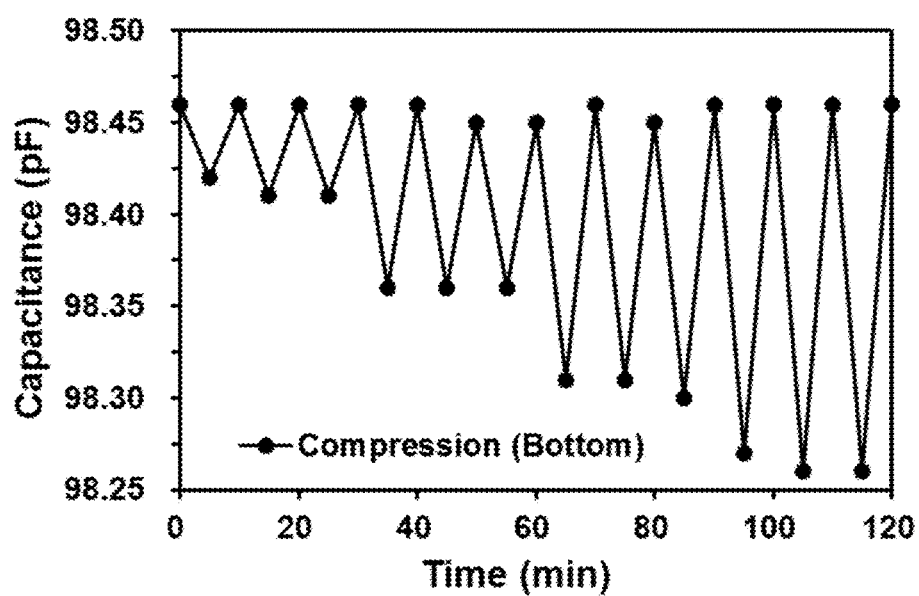
FIG. 5(c) shows the corresponding variation with time of the capacitance measured at the bottom surface. The capacitance measured at the bottom surface also decreases upon loading, such that the effect increases with increasing stress amplitude.

FIG. 5 shows the testing results for configuration I (FIGS. 4(a) and 4(b)). Specifically, FIG. 5 shows the effect of dynamic uniaxial compression on the capacitance. The stress ranges from 300 to 1500 Pa. As shown in FIG. 5(a), the stress amplitude is progressive increased, such that there are three cycles at each stress amplitude. As shown in FIG. 5(b), the capacitance measured at the top surface decreases upon compression, with the effect increasing with increasing stress amplitude. As shown in FIG. 5(c), the capacitance measured at the bottom surface also decreases upon compression, with the effect increasing with increasing stress amplitude. This decreasing trend of the capacitance is reasonable, based on the effect of the out-of-plane dimensional decrease upon uniaxial compression and the consequent decrease in the area of the in-plane capacitor.

Figure 6A:
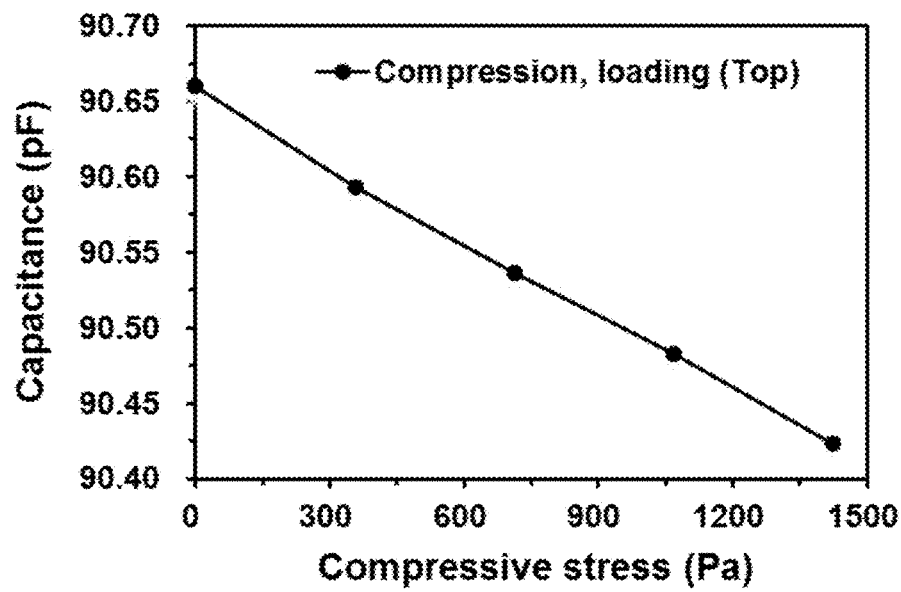
FIG. 6(a) shows the capacitance measured at the top surface.
Figure 6B:
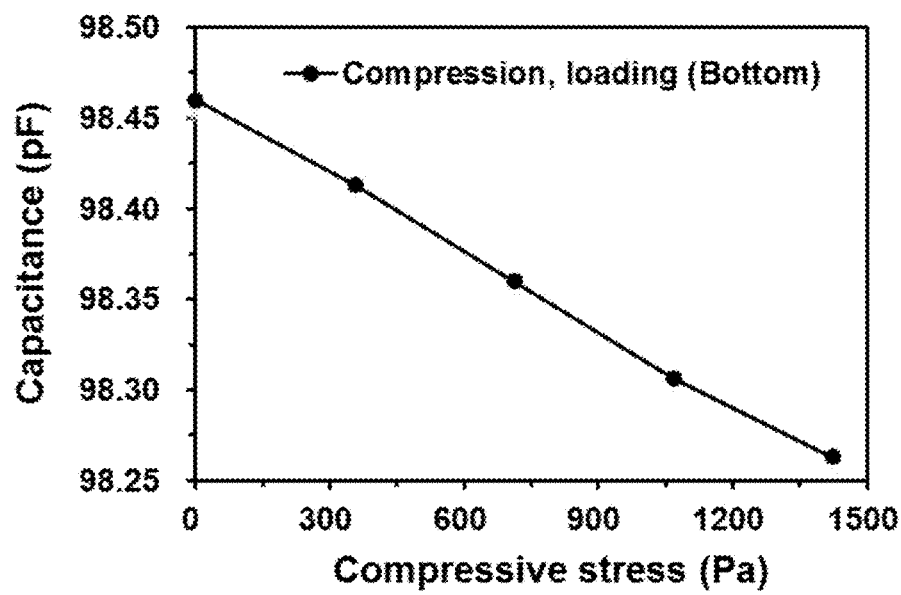
FIG. 6(b) shows the capacitance measured at the bottom surface.

FIG. 6 shows the variation of the capacitance with the compressive stress amplitude, which ranges from 300 to 1500 Pa, as obtained using configuration I (FIGS. 4(a) and 4(b)). Both the capacitance at the top surface and that at the bottom surface decrease upon compression, with the effect increasing with increasing stress. The relationship between capacitance and stress is essentially linear.

Figure 7A:
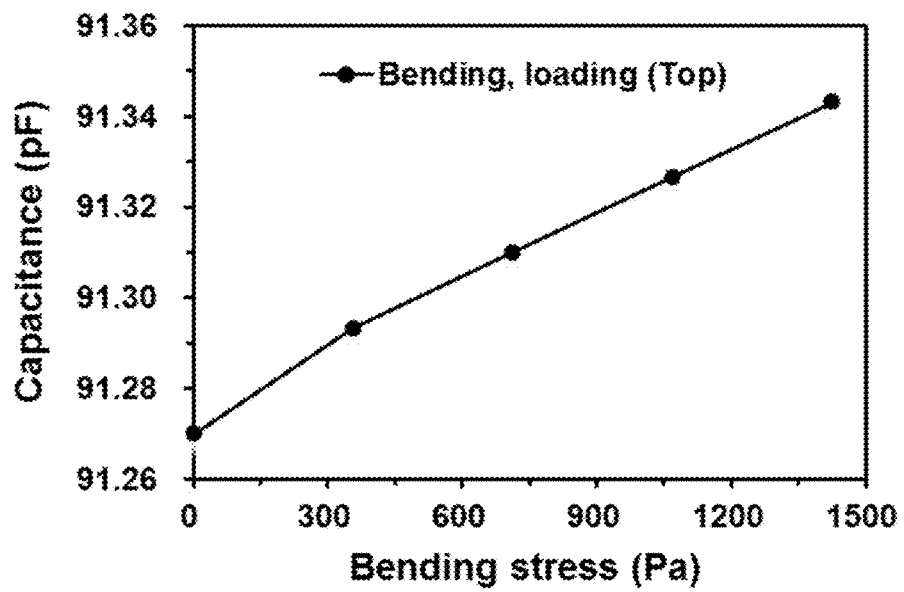
FIG. 7(a) shows the capacitance at the top surface.
Figure 7B:
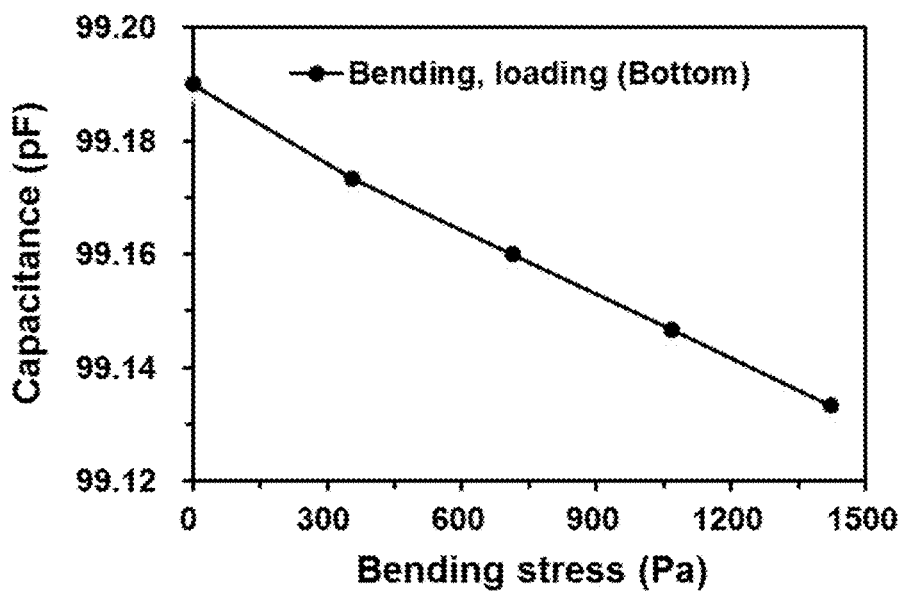
FIG. 7(b) shows the capacitance at the bottom surface.

FIG. 7 shows the variation of the capacitance with the flexural stress amplitude, which ranges from 300 to 1500 Pa, as obtained using configuration II (FIGS. 4(a) and 4(c)). A flexural stress of 4000 Pa corresponds to a normal stress of 75.2 Pa. The capacitance at the top surface increases upon flexure, with the effect increasing with increasing stress, whereas that at the bottom surface decreases upon flexure, with the effect increasing with increasing stress. These trends in the capacitance change are consistent with the effect of the in-plane dimensional changes upon flexure. At the top surface, which encounters in-plane compression, the decrease in the in-plane distance between the electrodes increases the capacitance. At the bottom surface, which encounters in-plane tension, the increase in the in-plane distance between the electrodes decreases the capacitance. For both the top and bottom surfaces, the relationship between capacitance and stress is essentially linear.

Figure 8A:
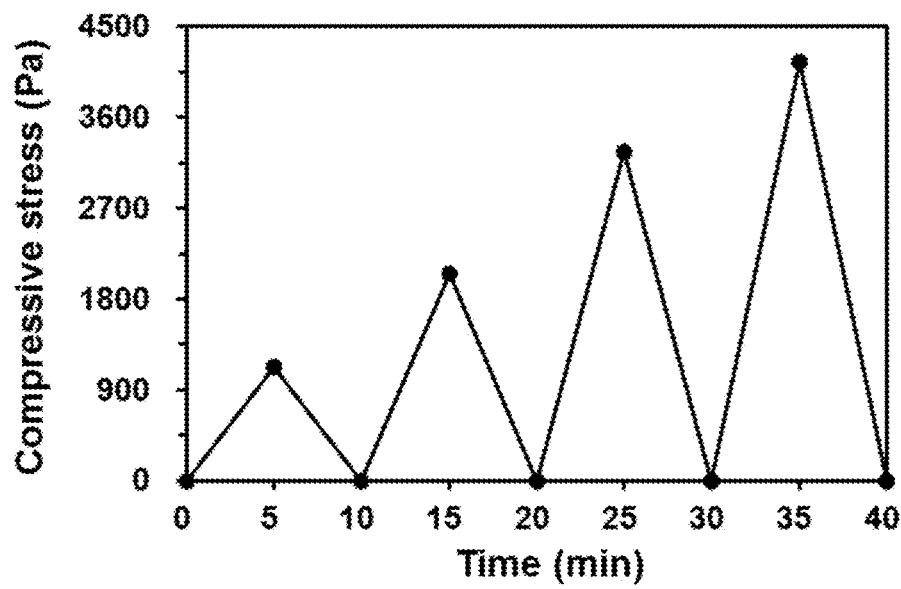
FIG. 8(a) shows the variation of the compressive stress with time. The stress amplitude is progressive increased, such that there is one cycle at each stress amplitude.
Figure 8B:
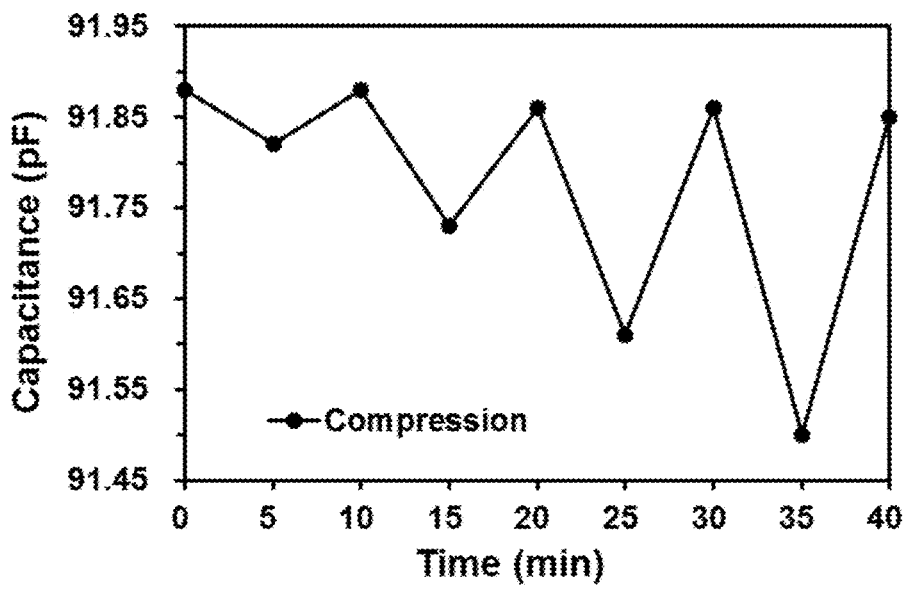
FIG. 8(b) shows the corresponding variation with time of the capacitance measured at the top surface. The capacitance decreases upon loading, such that the effect increases with increasing stress amplitude.

FIG. 8 shows the effect of dynamic uniaxial compression on the capacitance, as investigated using configuration I (FIGS. 4(a) and 4(b)). The stress amplitude ranges from 900 Pa to 4500 Pa. The stress amplitude is progressive increased, such that there is one cycle at each stress amplitude. The capacitance measured at the top surface decreases upon compression, with the effect increasing with increasing stress amplitude. The effect of the compressive stress on the capacitance is consistent with that shown in FIGS. 5 and 6.

Figure 9A:
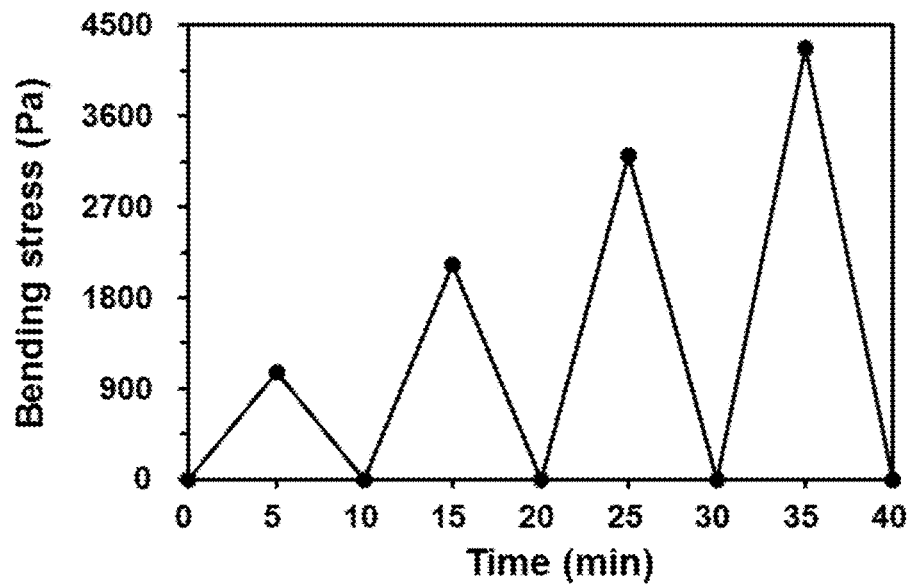
FIG. 9(a) shows the variation of the flexural (bending) stress with time. The stress amplitude is progressive increased, such that there is one cycle at each stress amplitude.
Figure 9B:
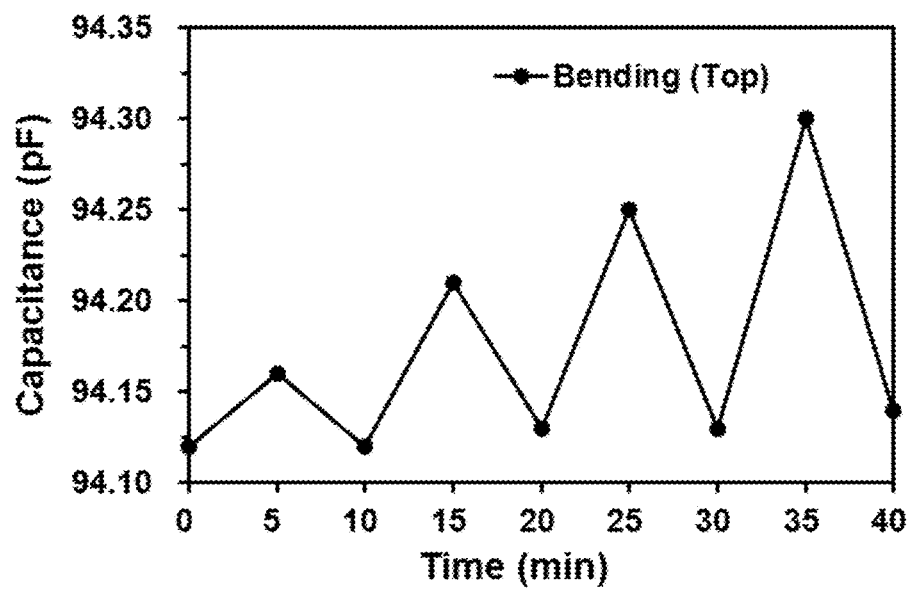
FIG. 9(b) shows the corresponding variation with time of the capacitance measured at the top surface. The capacitance measured at the top surface increases upon loading, such that the effect increases with increasing stress amplitude.
Figure 9C:
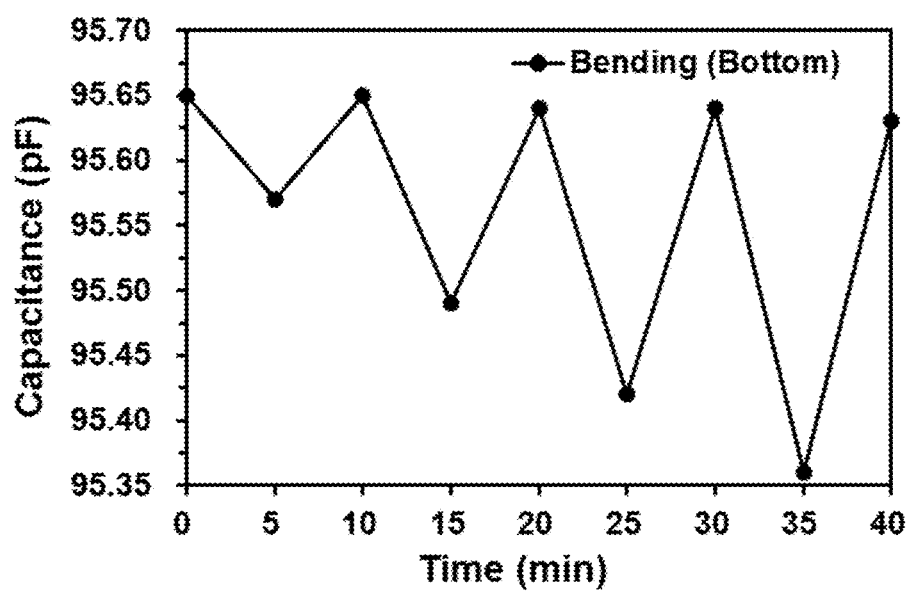
FIG. 9(c) shows the corresponding variation with time of the capacitance measured at the bottom surface. The capacitance measured at the bottom surface decreases upon loading, such that the effect increases with increasing stress amplitude.

FIG. 9 shows the effect of dynamic flexure on the capacitance, as investigated using configuration II (FIGS. 4(a) and 4(c)). The flexural stress amplitude ranges from 900 Pa to 4500 Pa. A flexural stress of 4000 Pa corresponds to a normal stress of 75.2 Pa. The stress amplitude is progressively increased, such that there is one cycle at each stress amplitude, as shown in FIG. 9(a). The capacitance measured at the top surface increases upon flexure, with the effect increases with increasing stress amplitude (FIG. 9(b)), whereas that measured at the bottom surface decreases upon flexure, with the effect increasing with increasing stress amplitude (FIG. 9(c)).

Figure 10:
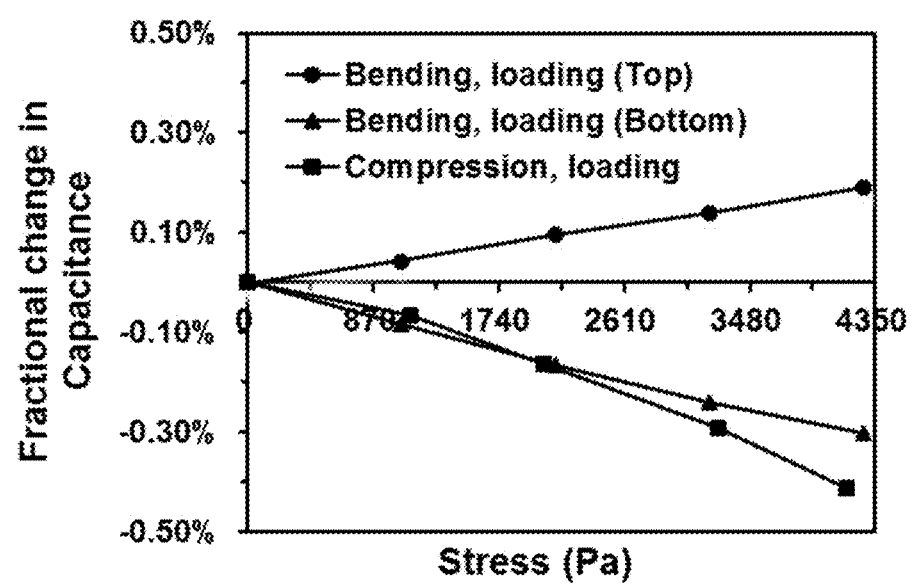
FIG. 10 shows the fractional change in capacitance vs. stress upon loading at progressively increasing stress amplitude in the low-stress regime. The results correspond to those in FIG. 6 for compression (configuration I, FIGS. 4(a) and 4(b)) and FIG. 7 for flexure (configuration II, FIGS. 4(a) and 4(c)). The stress shown for flexure (bending) is the flexural stress rather than the normal stress. A flexural stress of 4000 Pa corresponds to a normal stress of 75.2 Pa.

FIG. 10 shows the fractional change in capacitance vs. the stress amplitude upon loading at progressively increasing stress amplitude. The results correspond to those in FIG. 6 for compression (configuration I, FIGS. 4(a) and 4(b)) and FIG. 7 for flexure (configuration II, FIGS. 4(a) and 4(c)). For the same flexural stress, the fractional increase in capacitance at the top surface upon bending is less than the fractional decrease in capacitance at the bottom surface upon bending. For the same stress, the fractional decrease in capacitance at the top surface upon compression is comparable to the fractional decrease in capacitance at the bottom surface upon flexure.

Figure 11A:
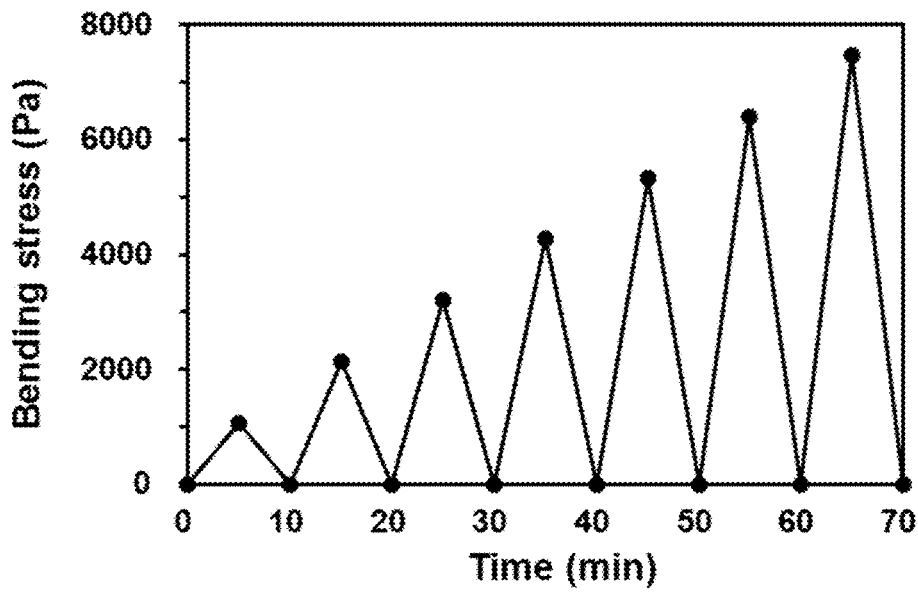
FIG. 11(a) shows the variation of the flexural stress (not the normal stress) with time. The stress amplitude is progressive increased, such that there is one cycle at each stress amplitude.
Figure 11B:
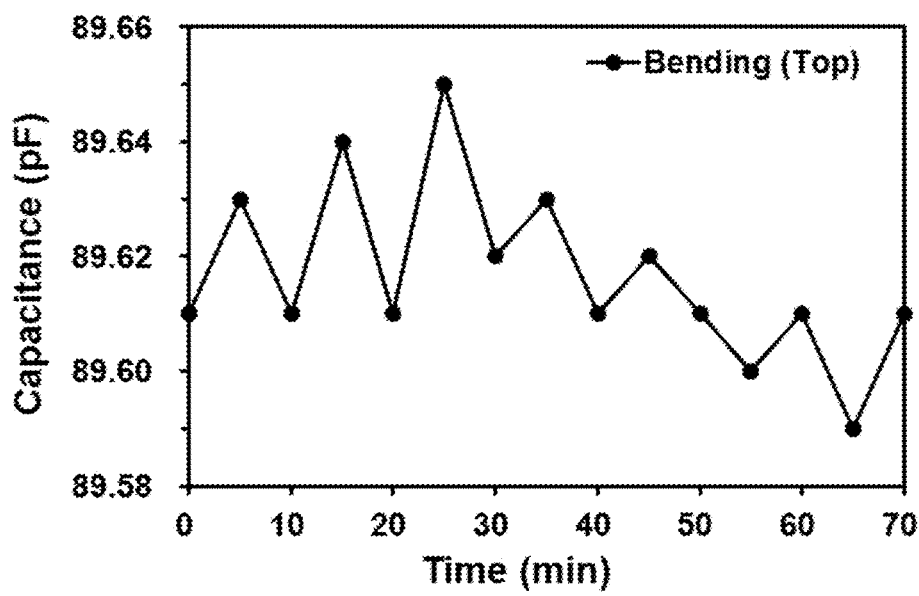
FIG. 11(b) shows the corresponding variation with time of the capacitance measured at the top surface. The capacitance measured at the top surface increases upon loading, such that the effect increases with increasing flexural stress amplitude up to 3100 Pa, but, above a flexural stress amplitude of 3100 Pa, it decreases upon loading, such that the effect increases with increasing flexural stress amplitude for stress amplitudes up to 7400 Pa and beyond.
Figure 11C:
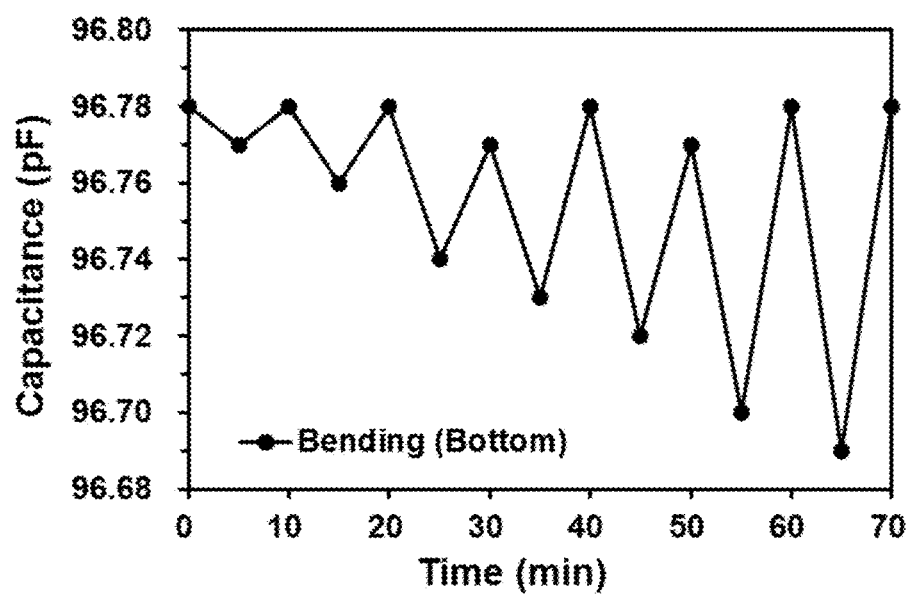
FIG. 11(c) shows the corresponding variation with time of the capacitance measured at the bottom surface. The capacitance decreases upon loading, such that the effect increases with increasing flexural stress amplitude for all stress amplitudes up to 7400 Pa and beyond.

FIG. 11 shows the effect of dynamic flexure on the capacitance, as investigated using configuration II (FIGS. 4(a) and 4(c)). The flexural stress ranges from 1000 Pa to 7400 Pa. A flexural stress of 4000 Pa corresponds to a normal stress of 75.2 Pa. The stress amplitude is progressive increased, such that there is one cycle at each stress amplitude, as shown in FIG. 11(a). The capacitance measured at the top surface increases upon loading, such that the effect increases will increasing stress amplitude up to 3100 Pa, as shown in FIG. 11(b). Moreover, the capacitance measured at the top surface increases upon loading for stress amplitudes up to 5200 Pa, though the effect decreases with increasing stress amplitude from 3100 Pa to 5200 Pa. However, it decreases upon loading for stress amplitude above 5200 Pa and beyond, such that the effect increases with increasing stress amplitude, as also shown in FIG. 11(b). In contrast, the capacitance measured at the bottom surface decreases upon loading, such that the effect increases monotonically with increasing stress amplitude for the entire range of the stress amplitude up to 7400 Pa.

The change of the top-surface capacitance from increasing upon loading at flexural stress amplitudes below 5200 Pa to decreasing upon loading at flexural stress amplitudes above 5200 Pa (FIG. 11(b)) is attributed to the compressive deformability of the region near the top surface when the flexural stress is above 5200 Pa and the consequent behavior of the top surface region that is akin to that under uniaxial compression (configuration I, FIGS. 4(a) and 4(b)), for which the capacitance decreases upon compressive loading, with the effect increasing with increasing compressive stress. A flexural stress of 4000 Pa corresponds to a normal stress of 75.2 Pa.

The low-stress regime (up to about 4000 Pa in the normal stress) is relevant to people detection, as in HVAC-zone occupancy monitoring, whereas the high-stress regime (above about 4000 Pa in the normal stress) is relevant to cargo or vehicle detection, as in asset management and traffic monitoring.

Example 4

This Example pertains to the raw materials used in preparing the cement-based material used for testing a piezoelectric cement-based material system in terms of the effectiveness of the self-sensing of the force exerted on the cement-based material in the medium-stress (about 4-19 kPa in the normal stress) and high-stress regimes (above about 19 kPa in the normal stress). Portland cement (Type I, ASTM C150, from Lafarge Corp., Southfield, Mich.) is used. The cement-based material studied is cement paste; no aggregate is used. The water/cement ratio is 0.35.

A high-range water reducing agent (Glenium 3000NS, BASF Construction Chemicals) is used at 1.0% by mass of cement. The defoamer (Colloids Inc., Marietta, Ga., 1010, USA) is used at 0.13% (% of specimen volume). No other admixture is used.

Cement powder and water are mixed for 5 min using a rotary mixer with a flat beater. The cement mix is poured to an oiled plastic mold. After filling the mold, an external vibrator is used to facilitate compaction and diminish the air bubbles. The specimens are demolded after 24 h and then cured at a relative humidity of nearly 100% for 28 days. The demolded specimens are ground and burnished to ensure that the surfaces are smooth before capacitance measurement. The cement-based material specimens are in the form of square slabs of size 48 mm×48 mm×4.39 mm.

Example 5

This Example pertains to a method of testing a piezoelectric cement-based material system for the effectiveness of the self-sensing of the force exerted on the cement-based material in the medium-stress (about 4-19 kPa in the normal stress) and high-stress regimes (above about 19 kPa in the normal stress).

Figure 12A:
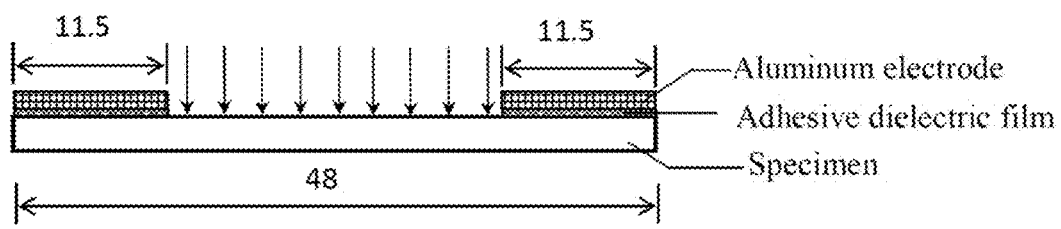
FIG. 12(a) shows the side view of testing configuration III (with support, which is not shown in FIG. 12(a), beneath the specimen throughout the area of normal force application, and the applied stress being uniaxially compressive).
Figure 12B:
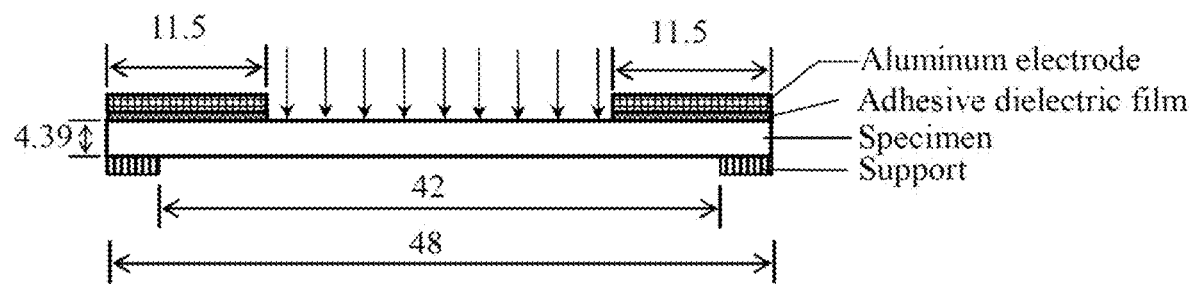
FIG. 12(b) shows the side view of testing configuration IV (with two parallel supports along two opposite edges of the specimen and the applied normal stress, which is shown by arrows in FIG. 12(b), providing flexure). The normal force at mid-span (i.e., the mid-point of the span, which is the distance between the two supports) in flexural testing, divided by the area of the normal force application, is the normal stress in the flexural testing. The normal stress is relevant to weighing, since the normal force relates to the weight to be determined in the weighing.
Figure 12C:
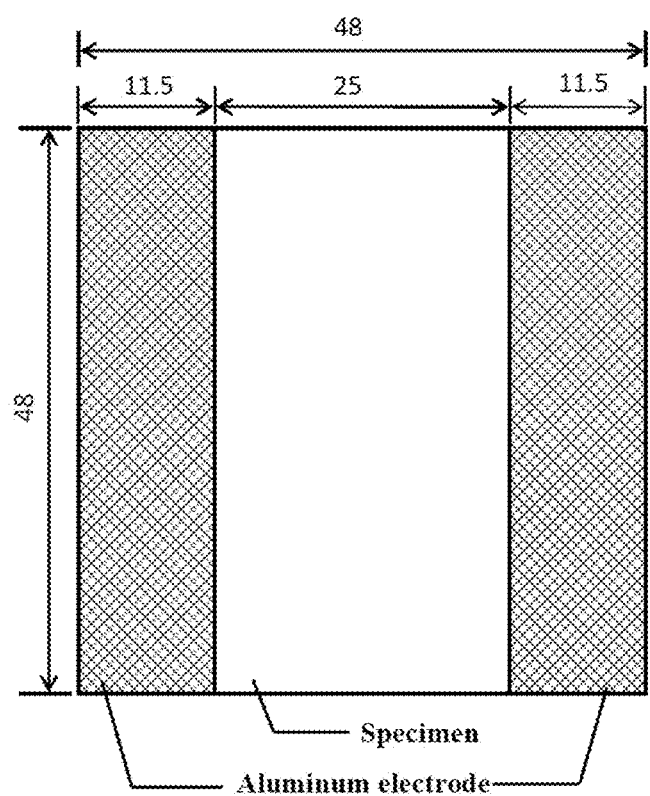
FIG. 12(c) shows the top view of either testing configuration (III or IV). A normal force is applied to the entirety of the area between the electrodes.
Figure 13A:
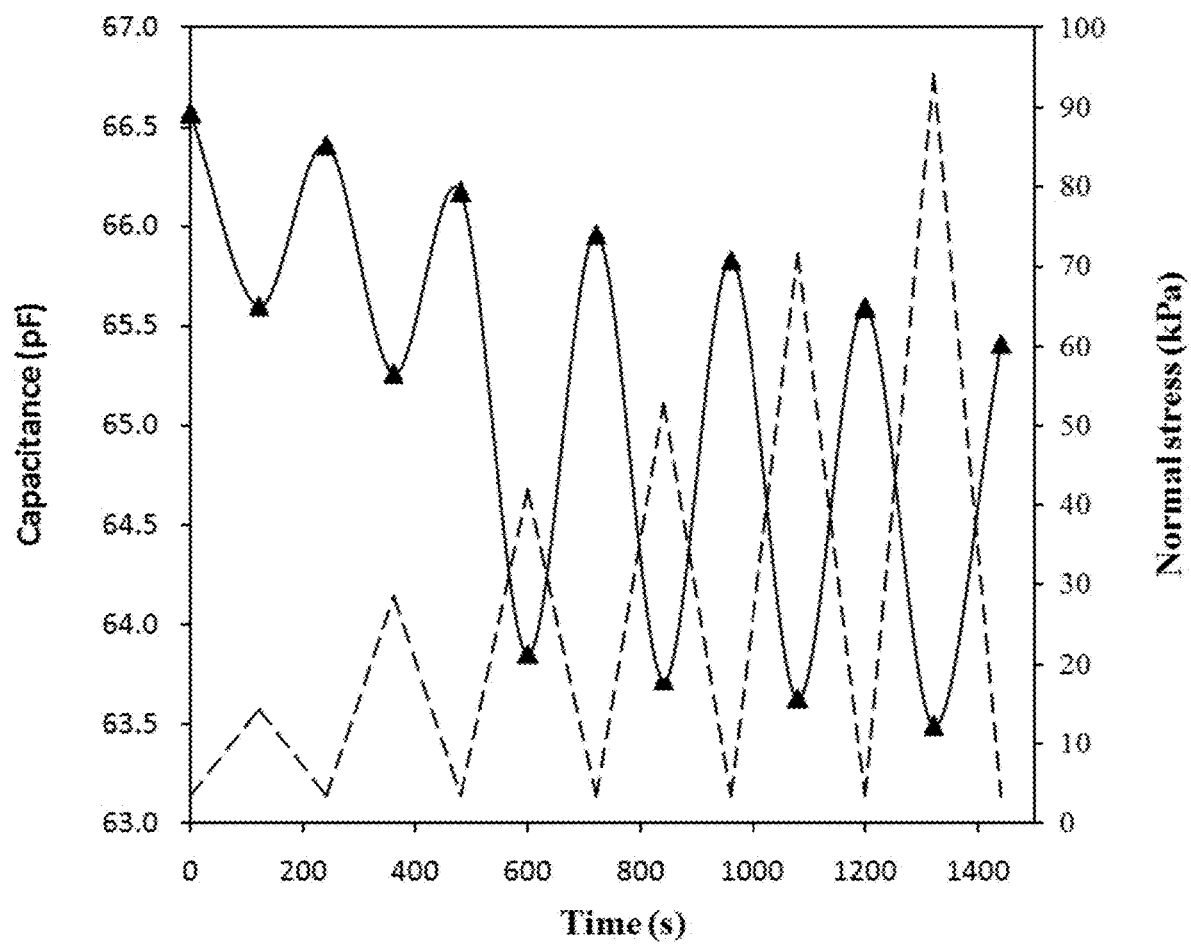
FIG. 13(a) shows the capacitance in the high-stress regime.
Figure 13B:
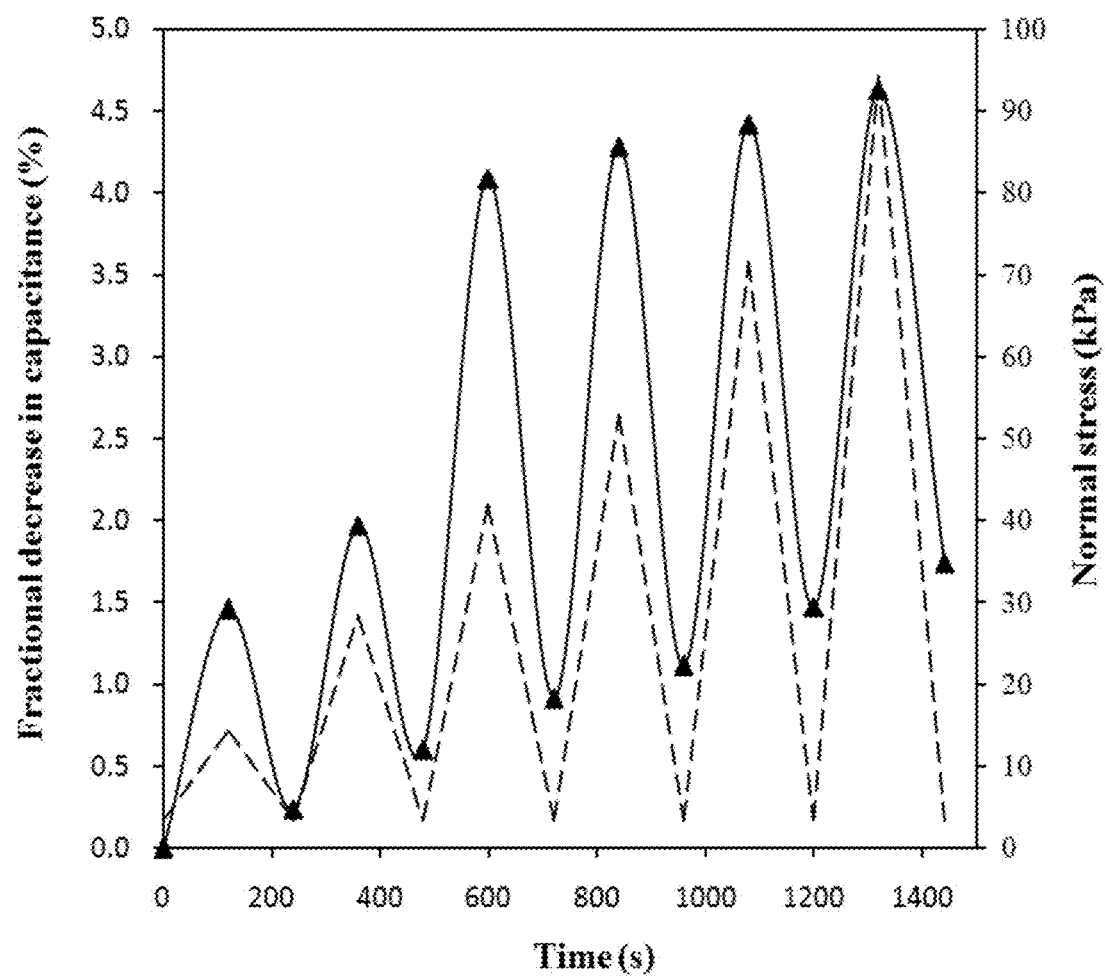
FIG. 13(b) shows the fractional decrease in capacitance in the high-stress regime.
Figure 13C:
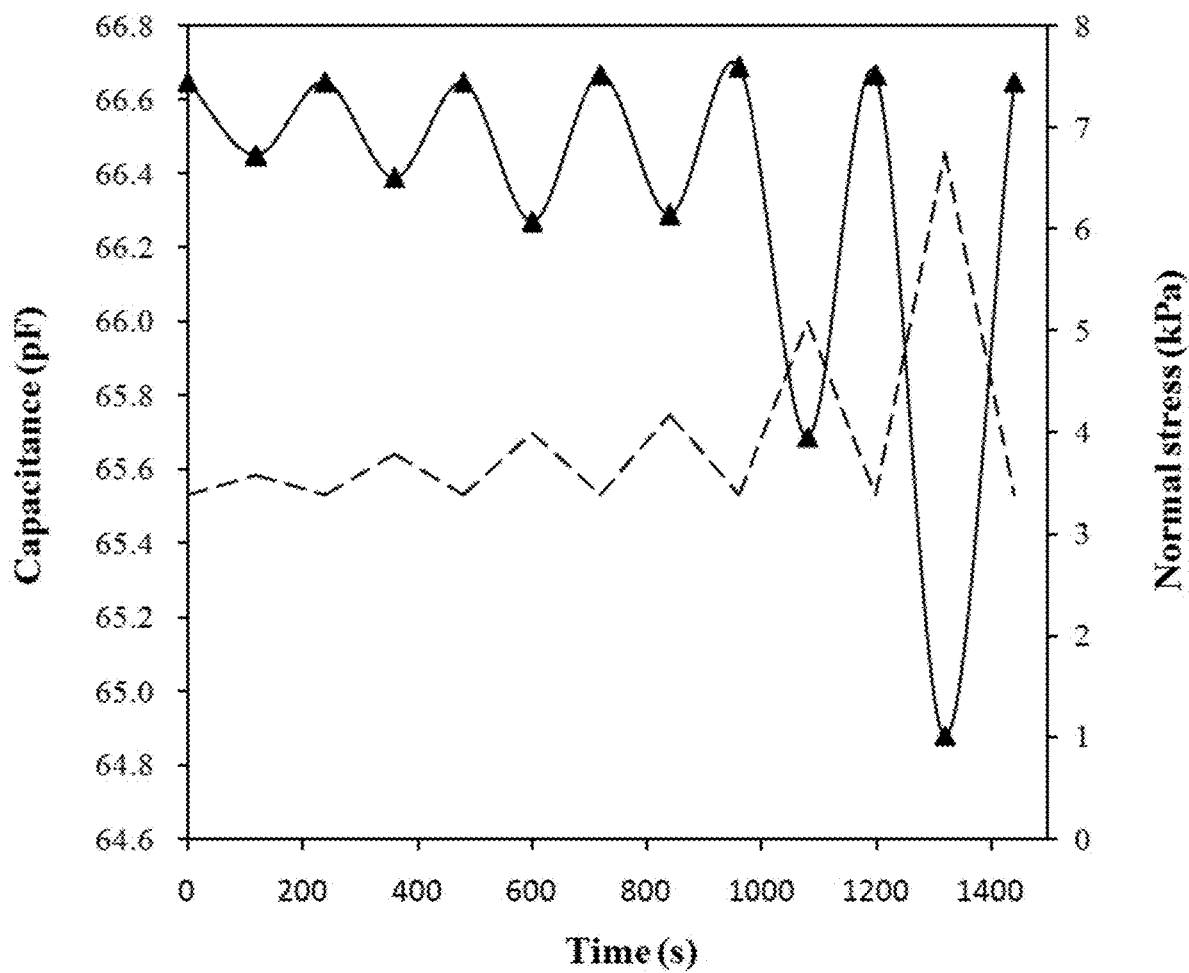
FIG. 13(c) shows the capacitance in the medium-stress regime.
Figure 13D:
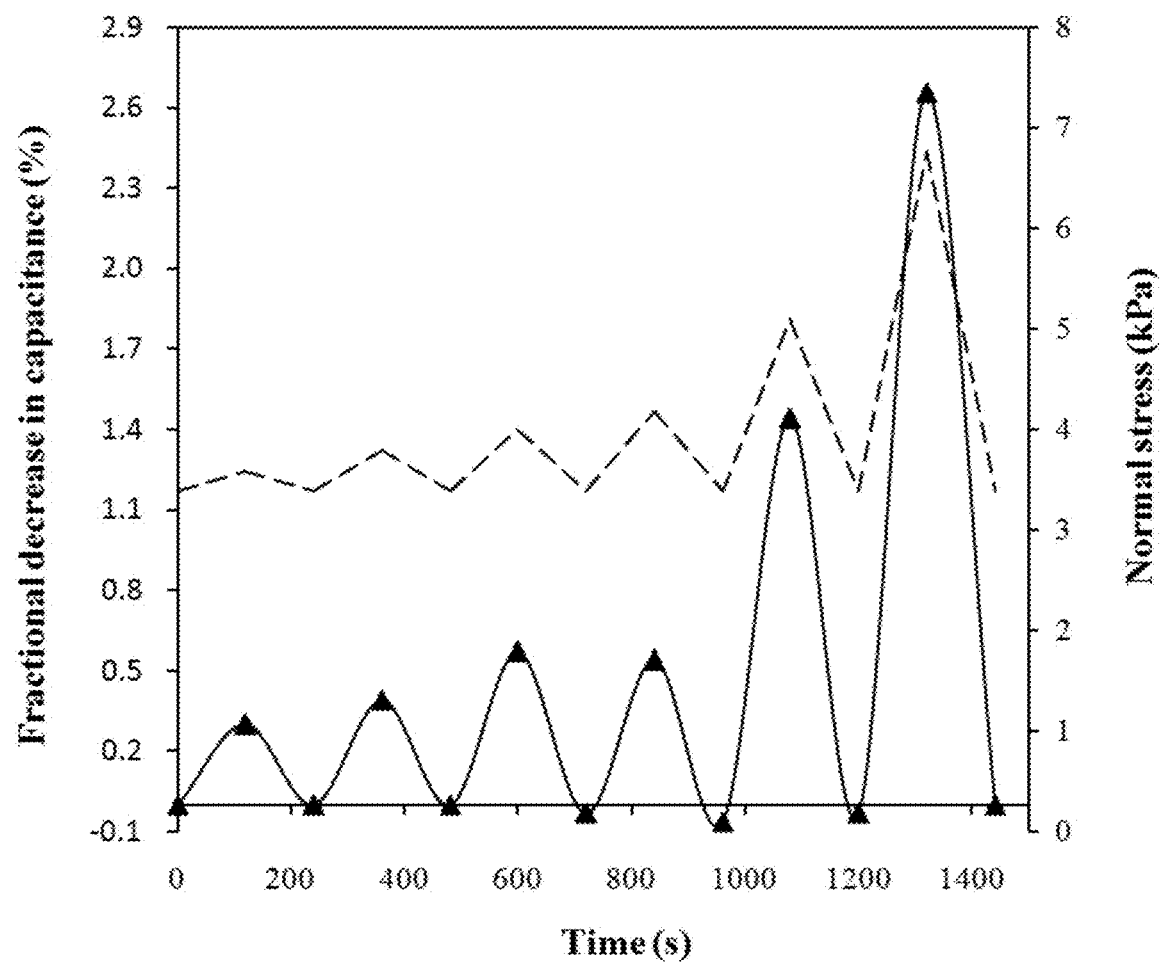
FIG. 13(d) shows the fractional decrease in capacitance in the medium-stress regime.

For measuring the in-plane capacitance, two electrodes on the same surface of the cement specimen, with their proximate edges separated by a distance of 25 mm, are used (FIG. 12). Aluminum foil is used as the electrode. A single layer of commercial double-sided adhesive tape (79 μm thick) is positioned between the aluminum foil (48 mm×11.5 mm) and the specimen in order to adhere the specimen to the electrode. The tape also serves as a dielectric film, which is used due to the fact that an RLC meter is not designed for measuring the capacitance of a conductor. Although the cement-based material is not conductive enough to require the dielectric film, the film is used in order to ensure stability in the measured capacitance.

In the stress sensing investigation, force in the direction perpendicular to the plane of the specimen is applied to the 48 mm×25 mm region between the two electrodes. The force is provided by using known weights positioned above this region. Two testing configurations are used. In configuration III (FIG. 12(a)), the specimen is supported beneath it throughout the area of normal force application, so that the applied normal stress is uniaxially compressive. In configuration IV (FIG. 12(b)), the specimen has two supports (48 mm×3 mm each) that are positioned along the two opposite edges of the specimen, so that this configuration involves flexure (bending). In both configurations, the minimum normal stress is 3.4 kPa.

The highest compressive stress of 283.4 kPa in the high-stress regime is within the elastic regime of the specimen. The compressive modulus is 2.92 GPa and the compressive strength is 57.9 MPa.

The capacitance is measured between the two electrodes, using a precision LCR meter (Instek LCR-816 High Precision LCR Meter, 100 Hz-2 kHz). The frequency used is 2.000 kHz. The electric field is in the plane of the specimen and corresponds to a voltage of 0.500 V over the distance of 25 mm between the proximate edges of the two electrodes. The capacitance reported is for the equivalent electrical circuit of a capacitance and a resistance in parallel.

Example 6

This Example pertains to the results of testing a piezo-electric cement-based material system for the effectiveness of the self-sensing of the force exerted on the cement-based material in the medium-stress (4-19 kPa in the normal stress) and high-stress regimes (above 19 kPa in the normal stress). In particular, this Example concerns configuration III (FIG. 12(a)), which is described in Example 5.

FIGS. 13 and 14 show the testing results for configuration III (FIG. 12(a)). Upon uniaxially compressive stress application, the capacitance is decreased. The greater is the stress, the more is the decrease in capacitance. The capacitance decrease is completely reversible in the medium-stress regime (FIGS. 13(c) and 14(c)), but is partly irreversible in the high-stress regime (FIGS. 13(a) and 14(a)). Moreover, the curve of capacitance vs. stress is more linear for the medium-stress regime than the high-stress regime, as shown by comparing FIGS. 14(a) and 14(c). The fractional decrease in capacitance due to the stress is up to 1.4% in the medium-stress completely-reversible regime (up to 19 kPa, FIG. 14(d)) and up to 6.5% in the high-stress partially-reversible regime (up to 280 kPa, FIG. 14(b)).

The in-plane capacitance decrease upon normal compressive stress application is in contrast to the separately observed through-thickness capacitance increase upon normal compressive stress (≥1.68 kPa) application. Furthermore, the in-plane capacitance decrease mentioned above is more significant, more reversible and more linear than the through-thickness capacitance increase This difference is attributed to the fact that the in-plane capacitance accentuates the region relatively close to the surface (due to the exponential decay of the electric field as it penetrates the specimen), whereas the through-thickness capacitance reflects the condition of the entire thickness. Furthermore, a decrease in the thickness upon normal compressive stress application decreases the area of the in-plane capacitor (hence decreasing the in-plane capacitance), but the thickness reduction increases the through-thickness capacitance.

Example 7

This Example pertains to the results of testing a piezo-electric cement-based material system for the effectiveness of the self-sensing of the force exerted on the cement-based material in the medium-stress (about 4-19 kPa in the normal stress) and high-stress regimes (above 19 kPa in the normal stress). In particular, this Example concerns configuration IV (FIG. 12(b)), which is described in Example 5.

FIGS. 15 and 16 show the testing results for configuration IV (FIG. 12(b)). As for configuration III (FIG. 12(a)), upon flexural stress application, the capacitance measured at the top surface is decreased. The greater is the stress, the more is the decrease in capacitance. This trend is consistent with that in FIG. 11(b) above 5.2 kPa of flexural stress. The capacitance decrease is completely reversible in the medium-stress regime (FIGS. 15(b) and 16(b)), but is partly irreversible in the high-stress regime (FIGS. 15(a) and 16(b)). Moreover, the curve of capacitance vs. stress is more linear for the medium-stress regime than the high-stress regime, as shown by comparing FIGS. 16(a) and 16(d). The fractional decrease in capacitance due to the stress is up to 5.3% in the high-stress regime (up to 280 kPa in the normal stress, FIG. 16(b)) and up to 2.4% in the medium-stress regime (up to 19 kPa in the normal stress, FIG. 16(e)).

Figure 16A:
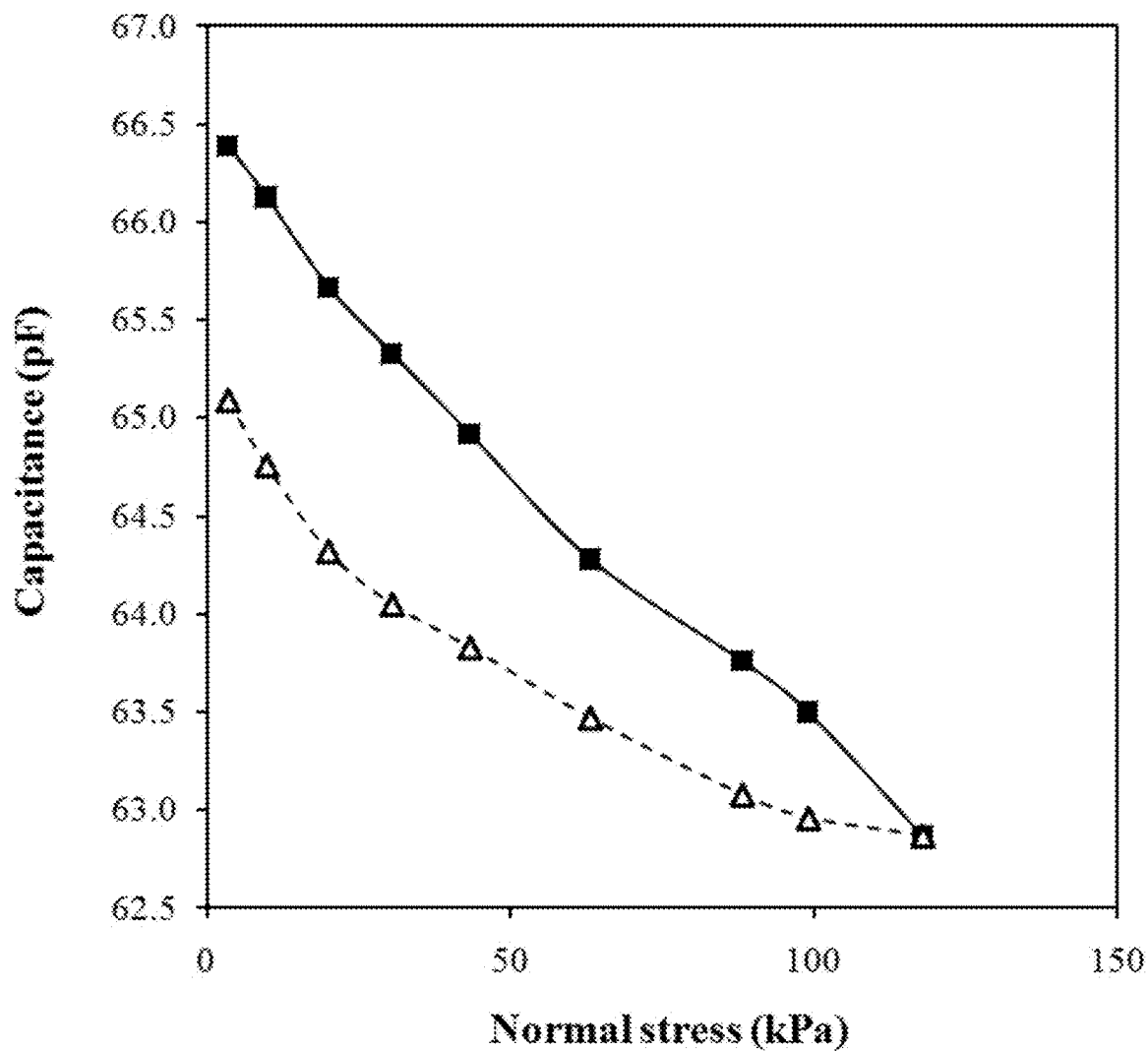
FIG. 16(a) shows the capacitance and the normal stress in the high-stress regime.
Figure 16B:
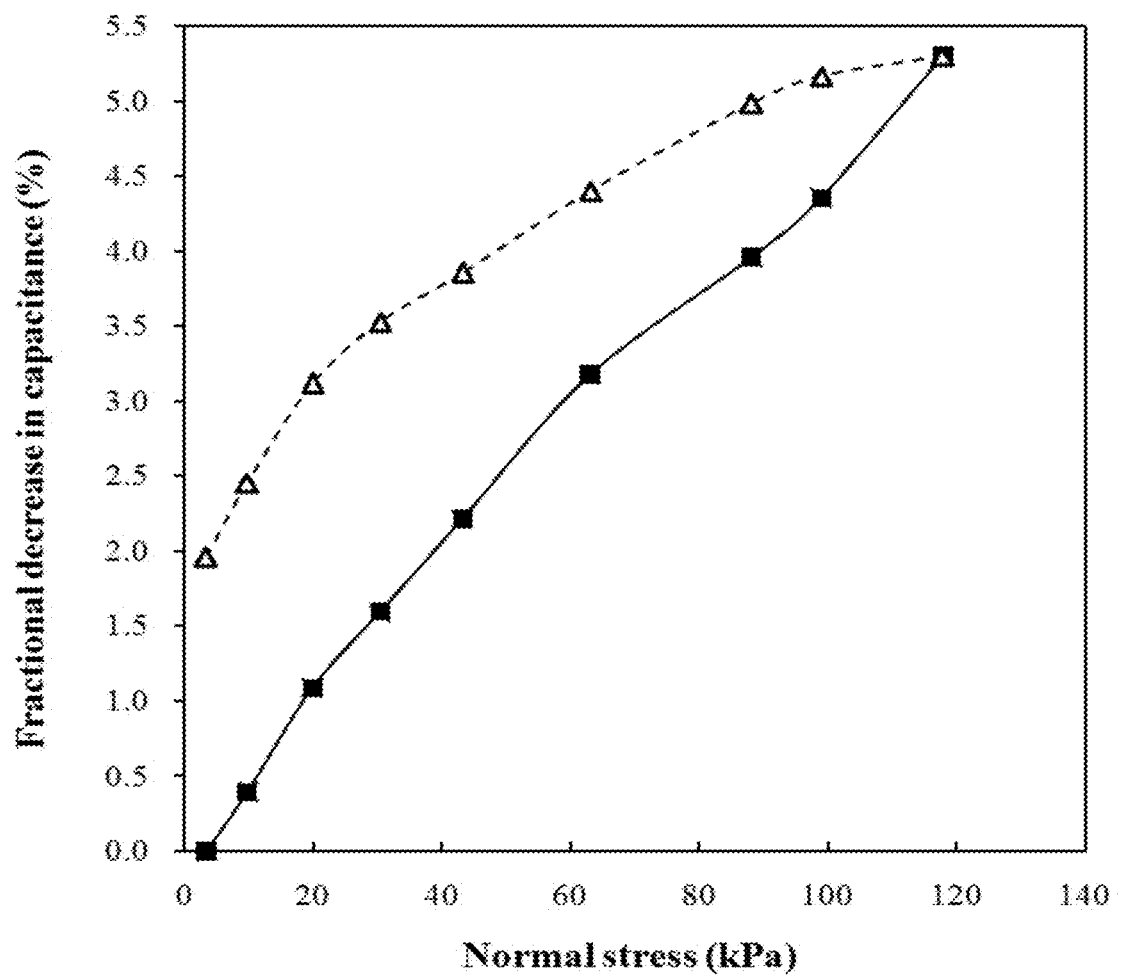
FIG. 16(b) corresponds to FIG. 16(a) and shows the fractional decrease in capacitance and the normal stress in the high-stress regime.
Figure 16C:
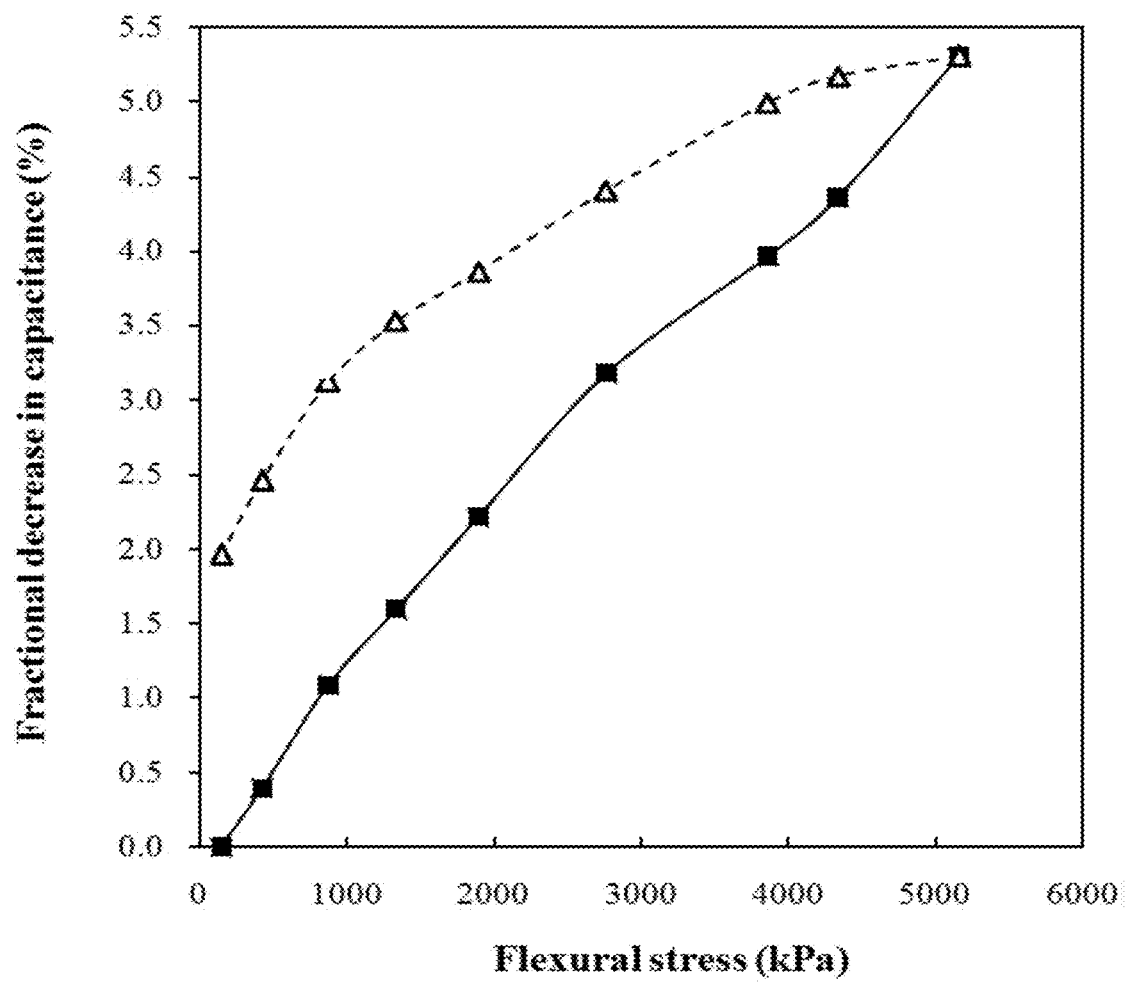
FIG. 16(c) corresponds to FIG. 16(b) and shows the fractional decrease in capacitance and the flexural stress (not the normal stress) in the high-stress regime.
Figure 16D:
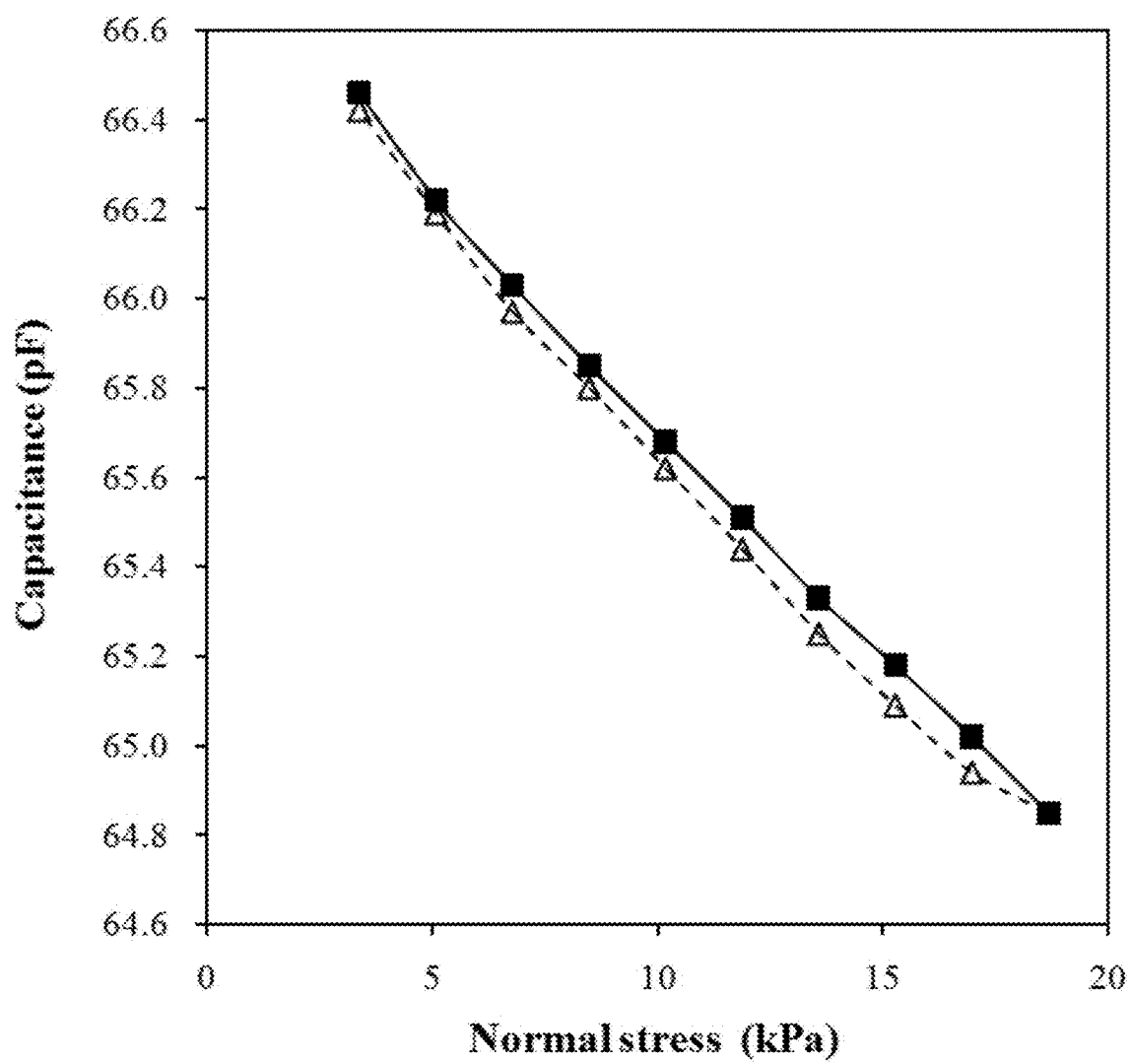
FIG. 16(d) shows the capacitance and the normal stress in the medium-stress regime.
Figure 16E:
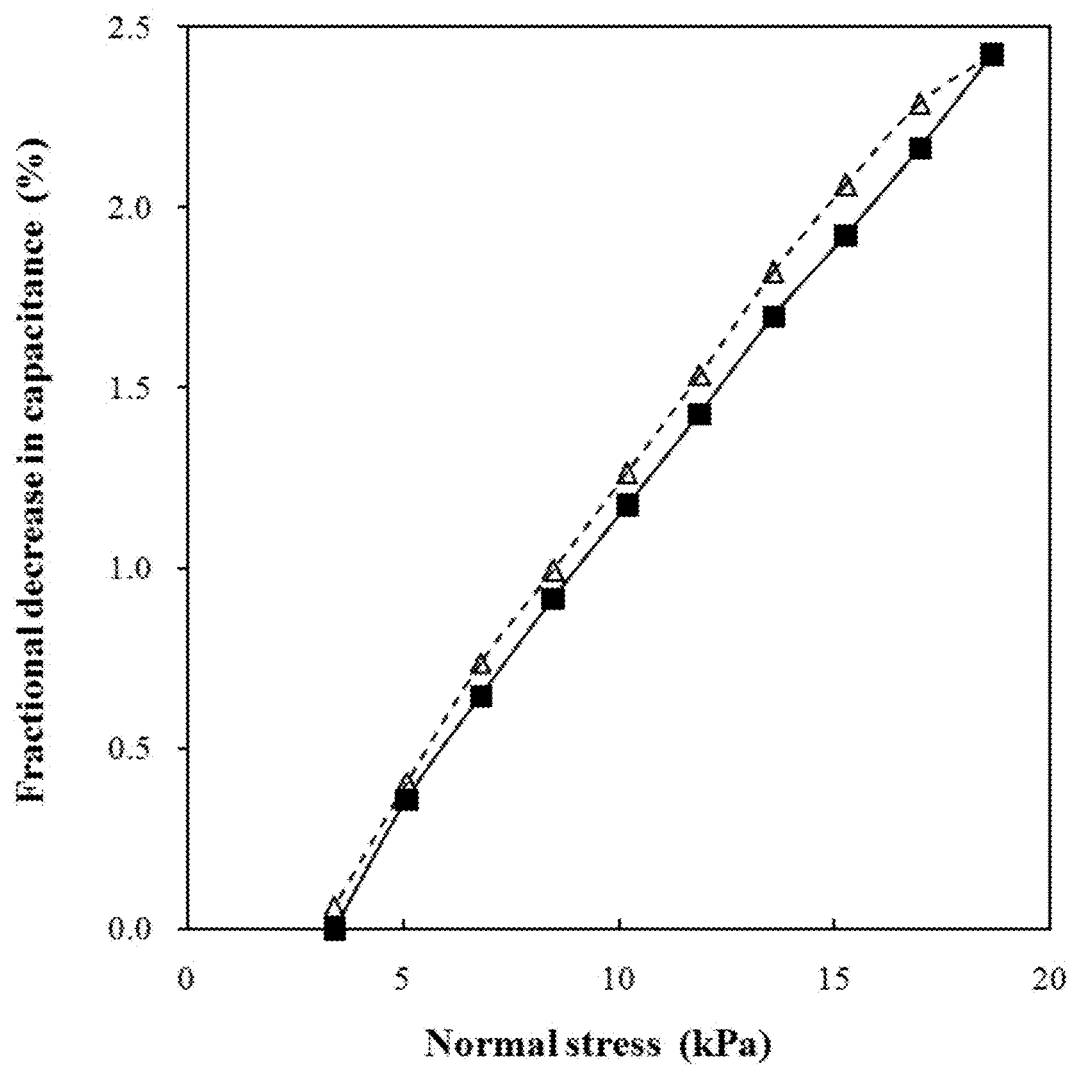
FIG. 16(e) corresponds to FIG. 16(d) and shows the fractional decrease in capacitance and the normal stress in the medium-stress regime.
Figure 16F:
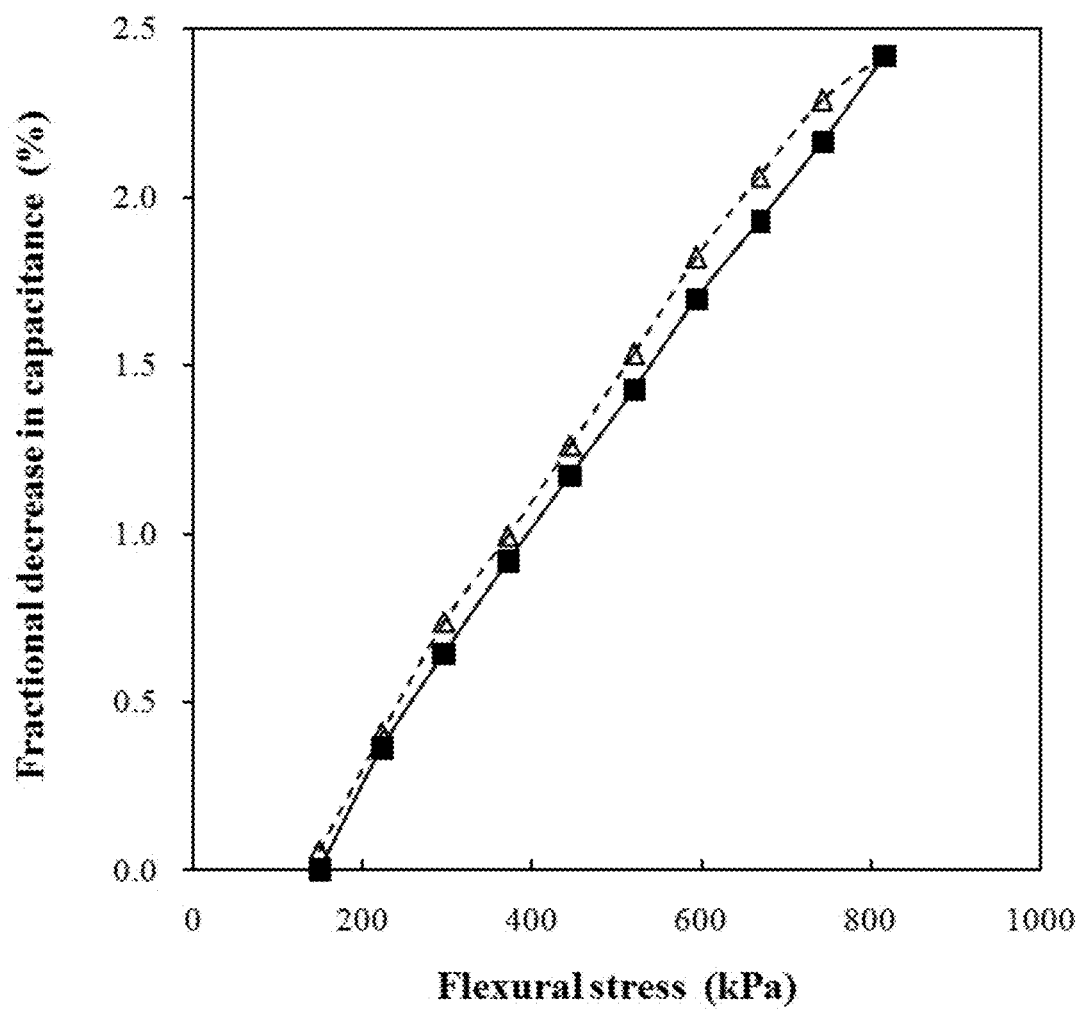
FIG. 16(f) corresponds to FIG. 16(e) and shows the fractional decrease in capacitance and the flexural stress (not the normal stress) in the medium-stress regime.

The flexural stress corresponding to the abovementioned normal stress is shown in FIGS. 16(c) and 16(f) for the high-stress and medium-stress regimes, respectively. In the high-stress regime, the highest normal stress of 118 kPa (FIG. 16(b)) corresponds to the highest flexural stress of 5100 kPa (FIG. 16(c)). In the medium-stress regime, the highest normal stress of 19 kPa (FIG. 16(e)) corresponds to the highest flexural stress of 800 kPa (FIG. 16(f)).

The applied stress in configuration IV (FIG. 12(b)) is flexural, which causes flexural stress that is compressive in the plane of the specimen slab in the top surface region of the slab and tensile in the plane of the slab in the bottom surface region. Since the electrodes are on the top surface, the effect is due to the in-plane compressive stress. If one assumes that the strain is responsible for the phenomenon, the in-plane compressive stress would cause the capacitance to increase, due to the decrease in thickness of the in-plane capacitor. However, the capacitance decreases, as in configuration III (FIG. 12(a)), in which the stress is uniaxially compressive in the direction perpendicular to the plane of the slab.

In case that the electrodes are on the bottom surface of the cement-based material specimen during flexure, the capacitance also increases upon flexure, as for the case of the electrodes being on the top surface of the specimen. The effect of flexure on the capacitance is essentially the same for the case of the electrodes on the bottom surface and the case of the electrodes on the top surface. The similarity in the trend of the capacitance decreasing with stress upon flexure for the top and bottom surfaces is because (i) the top surface experiences a degree of normal compression in the medium-stress and high-stress regimes, due to the deformability of the material in these regimes, and (ii) the bottom surface experiences flexural tension, which causes the thickness of the in-plane capacitor to increase.

Example 8

This Example pertains to the results of testing a piezoelectric cement-based material system for the effectiveness of the self-sensing of the force exerted on the cement-based material in the medium-stress (about 4-19 kPa in the normal stress) and high-stress regimes (above about 19 kPa in the normal stress). In particular, this Example concerns a comparison of the results obtained using configuration III (FIG. 12(a)) and those obtained using configuration IV (FIG. 12(b)). These configurations are described in Example 5

Figure 14A:
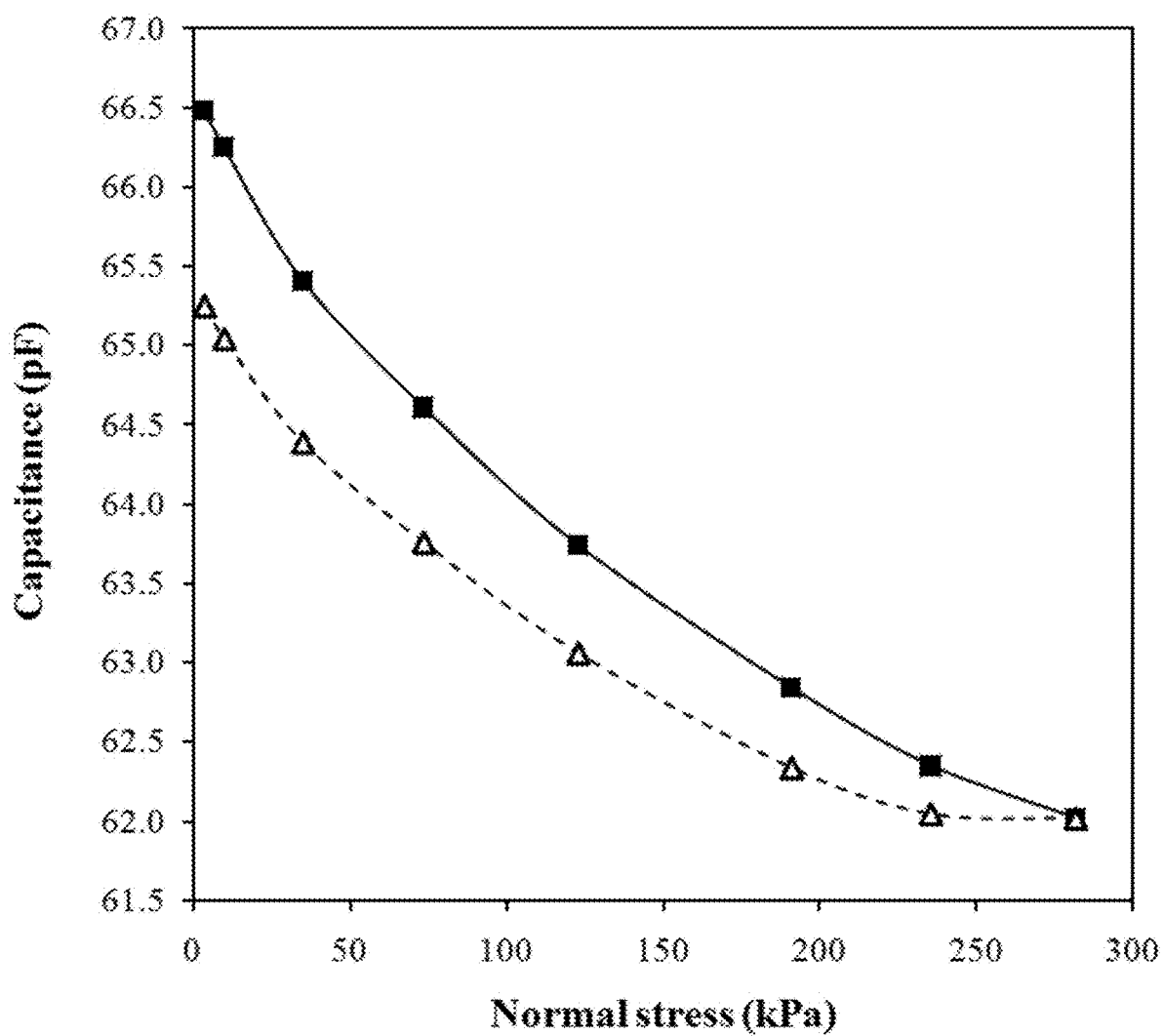
FIG. 14(a) shows the capacitance in the high-stress regime.
Figure 14B:
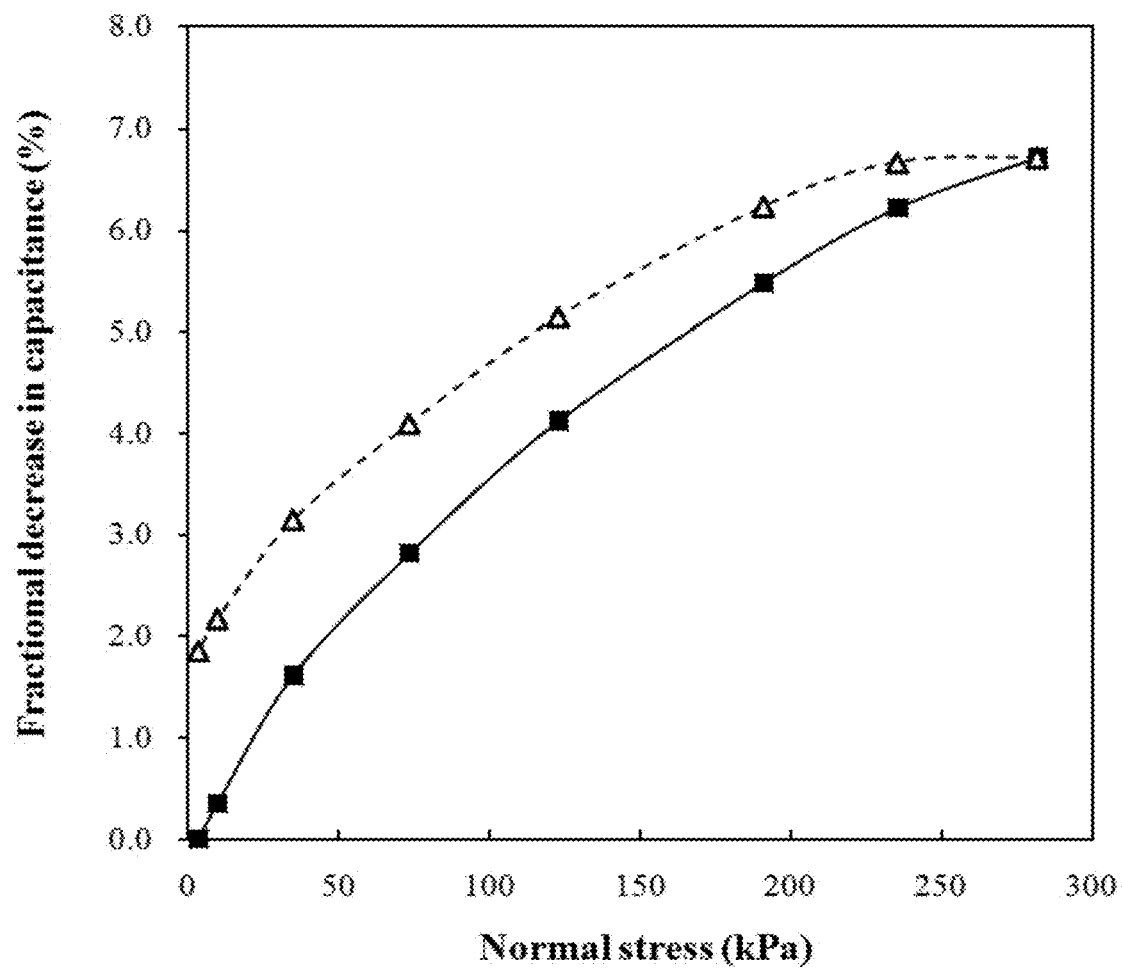
FIG. 14(b) shows the fractional decrease in capacitance in the high-stress regime.
Figure 14C:
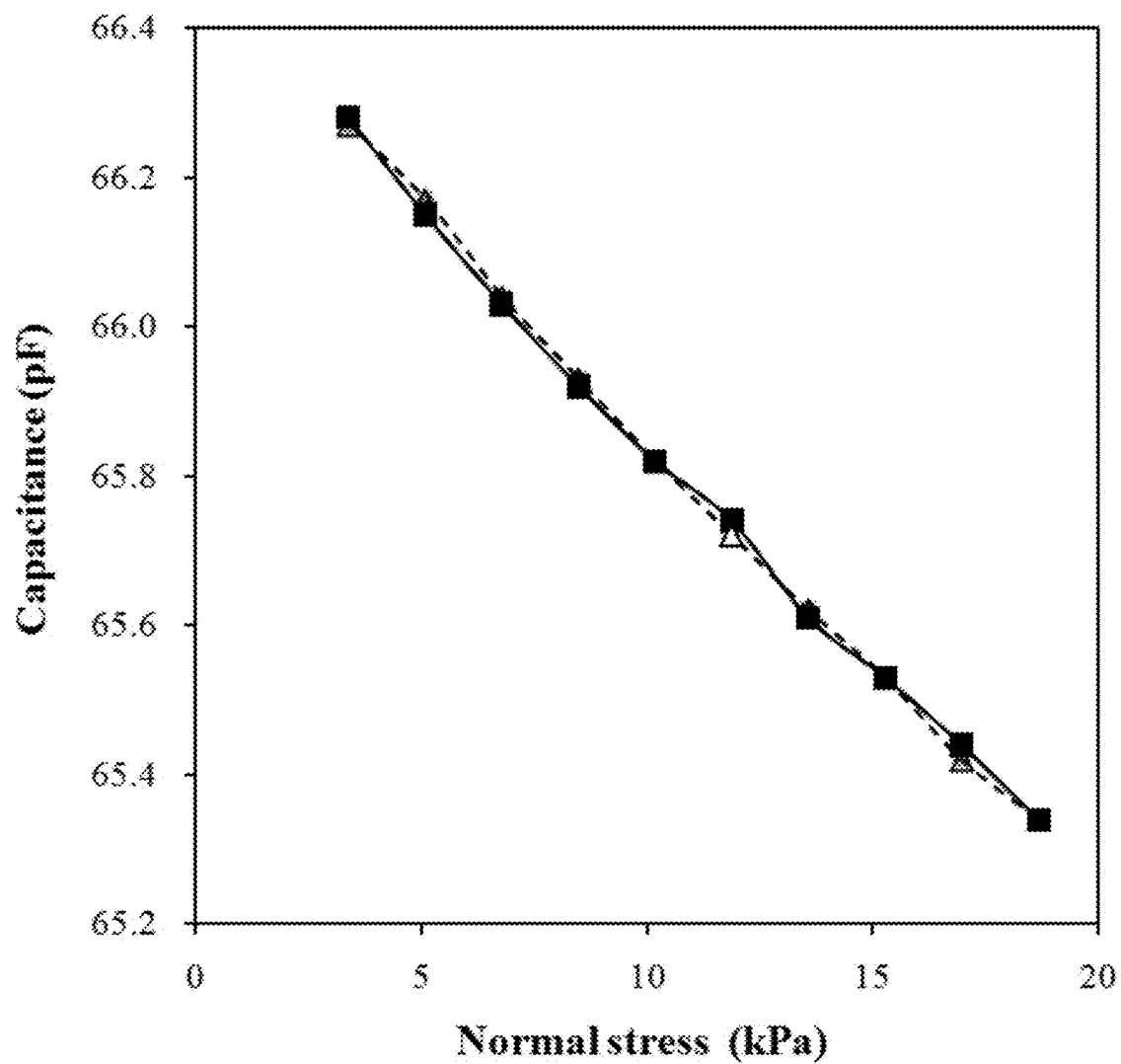
FIG. 14(c) shows the capacitance in the medium-stress regime.
Figure 14D:
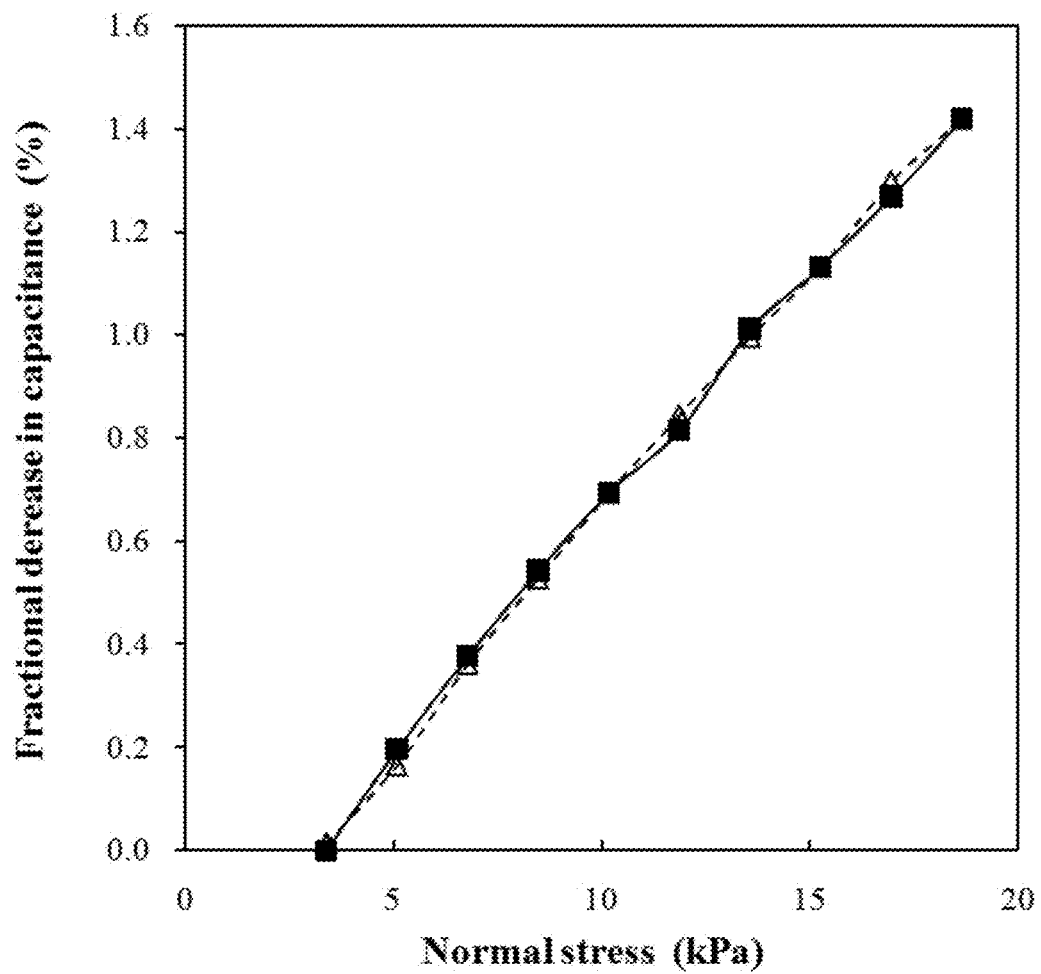
FIG. 14(d) shows the fractional decrease in capacitance in the medium-stress regime.
Figure 15A:
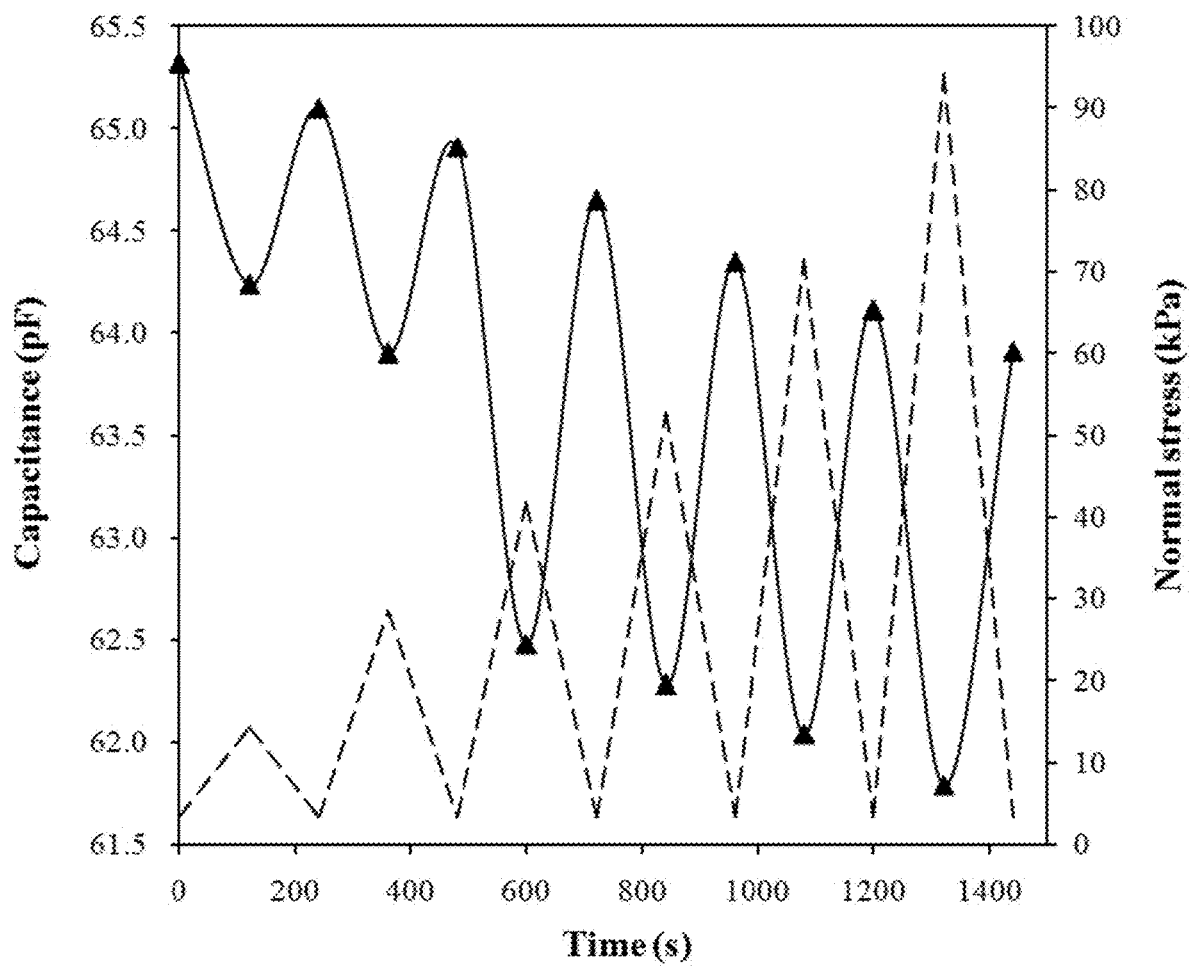
FIG. 15(a) shows the capacitance in the high-stress regime.
Figure 15B:
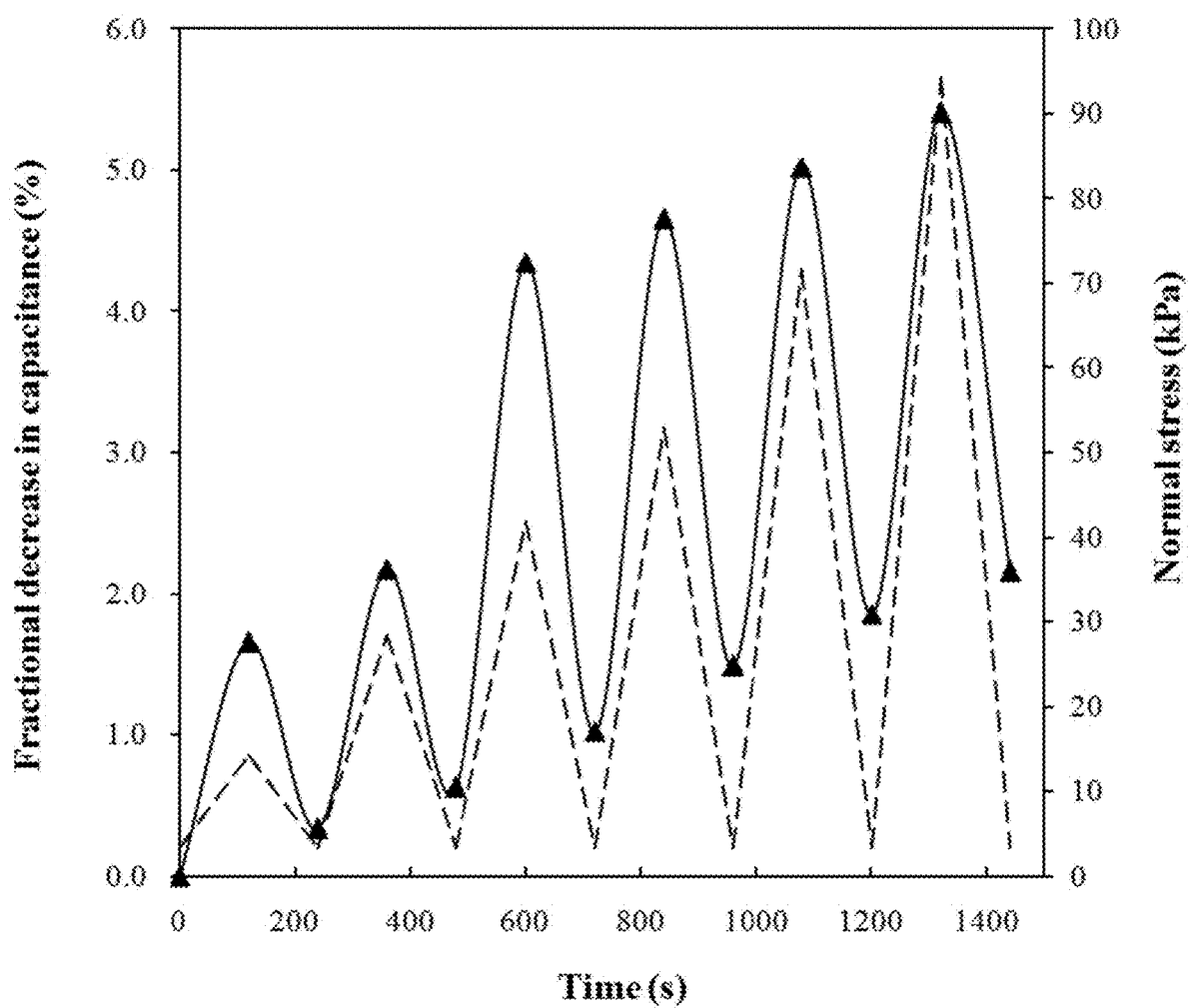
FIG. 15(b) shows the fractional decrease in capacitance in the high-stress regime.
Figure 15C:
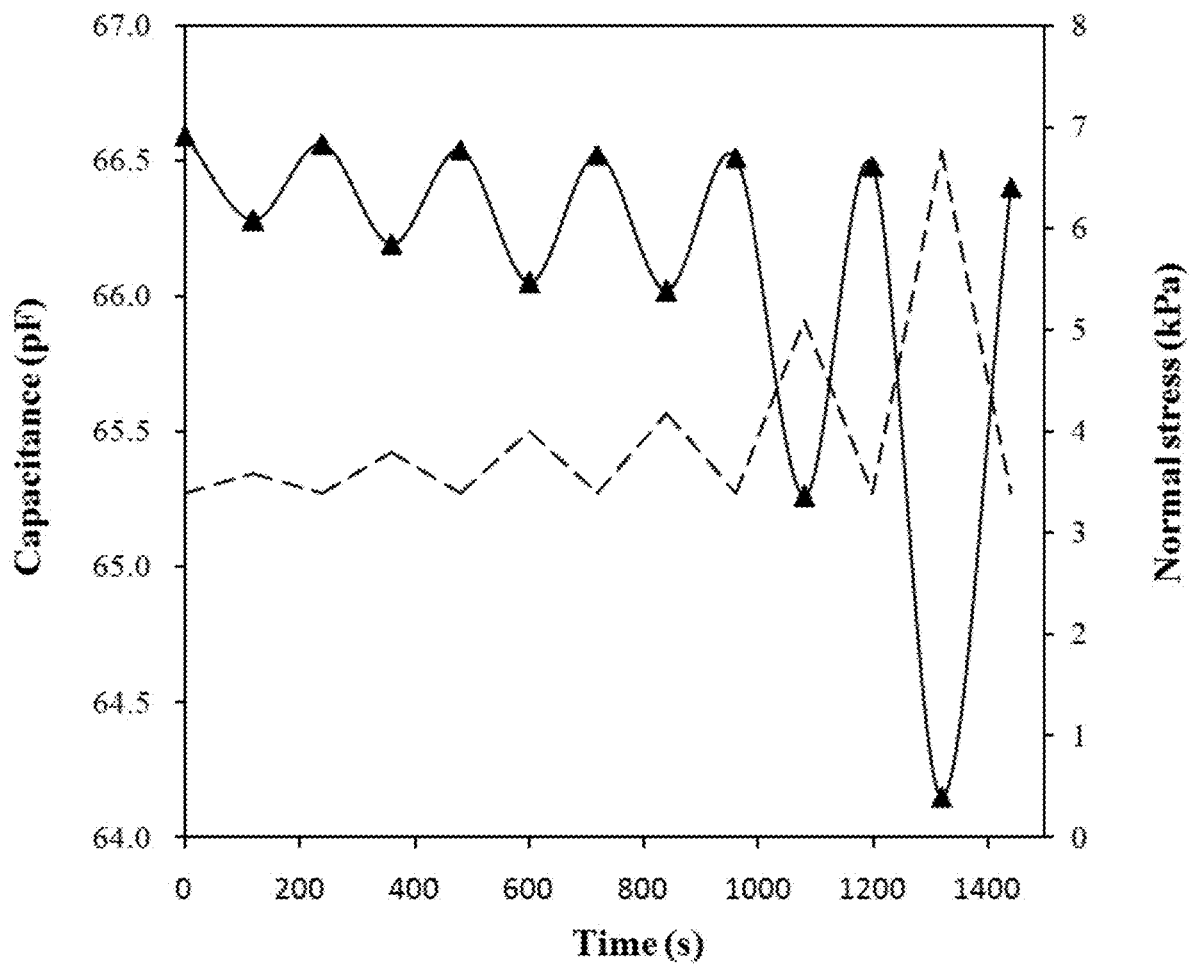
FIG. 15(c) shows the capacitance in the medium-stress regime.
Figure 15D:
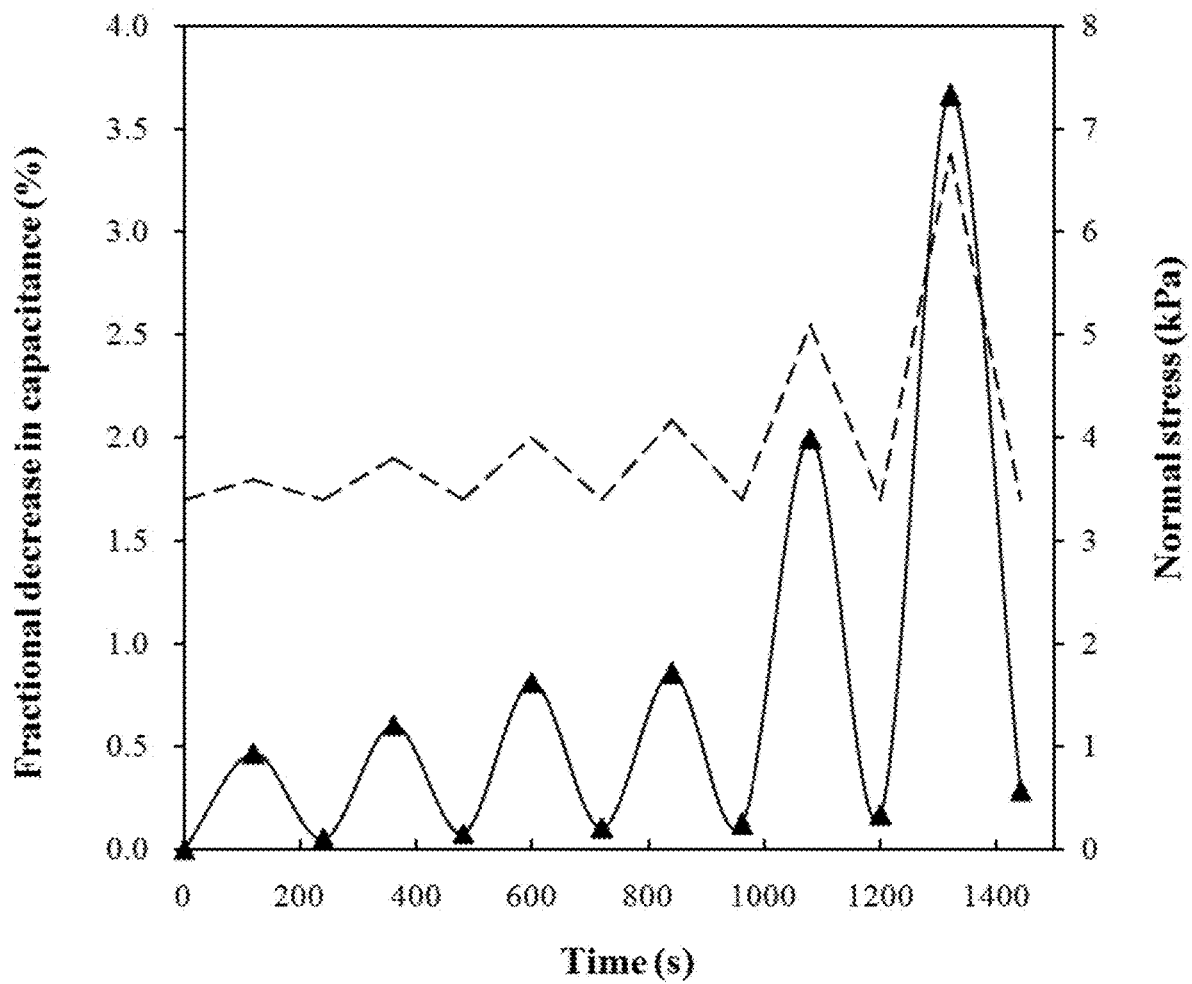
FIG. 15(d) shows the fractional decrease in capacitance in the medium-stress regime.

For configuration III (FIG. 12(a)), the fractional decrease in capacitance due to the normal stress of 19 kPa (medium-stress regime in which the capacitance change is completely reversible) is 1.4% (FIG. 14(d)). For configuration IV (FIG. 12(b)), the fractional decrease in capacitance due to the normal stress of 19 kPa (medium-stress regime in which the capacitance change is completely reversible) is 2.4% (FIG. 16(e)). This means that configuration IV (FIG. 12(b)) is more sensitive for the normal stress than configuration III (FIG. 12(a)) in the medium-stress regime.

For configuration III (FIG. 12(a)), the fractional decrease in capacitance due to the normal stress of 280 kPa (high-stress regime in which the capacitance change is partially reversible) is 6.5% (FIG. 14(b)). For configuration IV (FIG. 12(b)), the fractional decrease in capacitance due to the normal stress of 280 kPa (high-stress regime in which the capacitance change is partially reversible) is 5.3% (FIG. 16(b)). This means that configuration III (FIG. 12(a)) is more sensitive for the normal stress than configuration IV (FIG. 12(b)) in both medium-stress and high-stress regimes.

Instead of considering the fractional change in capacitance, one can consider the change in capacitance. The change in capacitance per unit normal stress change for configuration IV (FIG. 12(b)) is 0.031 pF/kPa (FIG. 16(a)) and 0.101 pF/kPa (FIG. 16(d)) for high-stress and medium-stress regimes, respectively. The value for configuration III (FIG. 12(a)) is 0.016 pF/kPa (FIG. 14(a)) and 0.061 pF/kPa (FIG. 14(c)) for high-stress and medium-stress regimes, respectively. The value is higher for configuration IV (FIG. 12(b)) than configuration III (FIG. 12(a)) in both regimes.

Comparison of FIGS. 14(c) and 16(d) shows that the curve of capacitance vs. normal stress is slightly more linear and slightly less hysteretic for configuration III (FIG. 12(a)) than configuration IV (FIG. 12(b)) in the medium-stress regime. However, comparison of FIGS. 14(a) and 16(a) shows that this curve is more linear for configuration IV (FIG. 12(b)) than configuration III (FIG. 12(a)) in the high-stress regime.

For both configurations III and IV, the sensitivity (in terms of the capacitance change per unit normal stress change) for the stress sensing is higher for the medium-stress regime than the high-stress regime. In addition, the linearity and reversibility are superior for the medium-stress regime. The lowest change in normal stress sensed is 0.2 kPa in both configurations. This corresponds to a flexural stress change of 8.5 kPa (configuration IV, FIG. 12(b)). This high sensitivity for low stress is comparable to that of carbon fiber cement that derives its sensing ability from its piezoresistive behavior (U.S. Pat. No. 5,817,944).

Example 9

This Example pertains to the science behind the results of testing a cement-based material system for the effectiveness of the self-sensing of the force exerted on the cement-based material. In particular, the science relates to how the stress affects the capacitance.

The electrical resistivity of the cement paste is $4.9 \times 10^5$ $\Omega \cdot cm$. Based on the resistivity and relative magnetic permeability (1, since the material is non-magnetic), the skin depth at 2 kHz (the frequency used in this work) is calculated to be 788 m, which much exceeds the specimen thickness in the testing shown here. Hence, the AC current injected from the specimen surface penetrates the complete thickness of the specimen, with negligible decay as it penetrates.

The highest normal compressive stress used in the testing in the high-stress regime is 280 kPa. With the elastic modulus of 2.92 GPa for the specimen material, the compressive strain in the specimen is $1 \times 10^{-4}$, which is much below the observed fractional decrease in capacitance. This means that the capacitance decrease cannot be explained by the compressive strain, even though a decrease in thickness would decrease the in-plane capacitance.

Given the relative permittivity κ of 24 for cement paste and the various dimensions in the testing configuration of this specification, the capacitance values and capacitance changes observed are much higher than the values expected by calculation based on the well-known equation $$C_v = \varepsilon_o \kappa A / l, \quad (1)$$

where $C_v$ is the capacitance due to the volume of the specimen that experiences the AC current, $\varepsilon_o$ is the permittivity of free space ($8.85 \times 10^{-12}$ F/m), A is the area of the in-plane current path (equal to the product of the depth d of current penetration and the width 146.50 mm of the electrode used in the low-stress regime testing, FIG. 4), and l is the thickness of the capacitor (approximately equal to the distance 119.12 mm between the proximate edges of the electrodes used in the low-stress regime testing, FIG. 4). For example, according to the calculation, the capacitance of 91.88 pF corresponds to d=352 mm (which is unreasonably large, since the specimen thickness is only 10.45 mm); the capacitance change of −0.38 pF corresponds to the change in d=−1.5 mm (also unreasonably large).

In the testing in the medium-stress and high-stress regimes (FIG. 12), l is the thickness of the capacitor (approximately equal to the distance 25 mm between the proximate edges of the electrodes). For example, according to the calculation, the capacitance of 66.28 pF corresponds to d=163 mm (which is unreasonably large, since the specimen thickness is only 4.39 mm); the capacitance change of −0.95 pF corresponds to the change in d=−2.33 mm (also unreasonably large).

The capacitance $C_i$ associated with the interface between each electrode and specimen is in series with $C_v$. Thus, the measured capacitance C is given by $$1/C = 2/C_i + 1/C_v. \quad (2)$$

Due to $C_i$ being not equal to infinity, $C_v > C$. Therefore, the consideration of $C_i$ causes the measured capacitance C to be an underestimate of $C_v$. This means that the issues of the capacitance and capacitance change being very high compared to the expectation based on Equation (1) are aggravated when Equation (2) is considered.

Due to the above arguments, the scientific origin of the high values of both capacitance and capacitance change observed is attributed to the piezoelectric effect, with the large change in capacitance upon stress application being due to the direct piezoelectric effect and the high capacitance in the absence of stress being related to the converse piezoelectric effect, which is associated with the AC electric field input from the LCR meter used to measure the capacitance. The occurrence of the piezoelectric effect in cement paste in the absence of any particular admixture is also supported by the observed increase of the through-thickness capacitance and through-thickness relative permittivity upon the application of a normal purely compressive stress ($\geq 1.68$ kPa).

Example 10

This Example pertains to practical considerations associated with the implementation of the cement-based material system of this invention for the self-sensing of the force exerted on the cement-based material.

In the testing in the low-stress regime, the distance between the proximate edges of the two electrodes is 119.12 mm (FIG. 4, Example 2). This distance can be changed over the range from 1 mm to 1 m. A smaller distance will increase the capacitance, thus making the change in capacitance also greater.

The flexural stress can be sensed by using electrodes positioned on the tensile or compressive surface of a concrete slab. The uniaxial compressive stress can also be sensed by using electrodes positioned on the top or bottom surface. This means that the electrodes can be on the floor (top surface) or the ceiling (bottom surface) in case that the slab is used as the floor slab of a multi-story building.

The capacitance measured at the bottom surface decreases with increasing flexural stress in the low-stress, medium-stress and high-stress regimes, whereas the capacitance measured at the top surface increases with increasing flexural stress in the low stress regime, but decreases with increasing flexural stress in the medium-stress and high-stress regimes. Therefore, interpretation of the results obtained under flexure is simpler for the capacitance measured at the bottom surface than that measured at the top surface. However, in case that the stress range is limited to either the low-stress regime or the combination of medium-stress and high-stress regimes, the interpretation of the results obtained under flexure is equally simple for the capacitances measured at the top and bottom surfaces.

In contrast to the resistance measurement that requires four electrical contacts for reliable piezoresistive measurement, the capacitance measurement involves only two electrodes. This further simplifies the practical implementation of the sensing technology.

Figure 17:
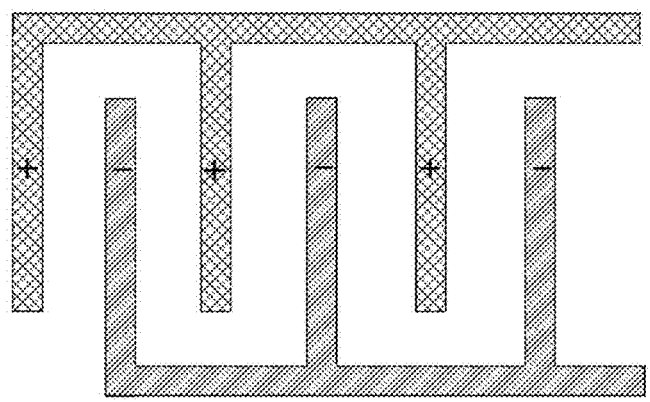
FIG. 17 illustrates a system of interdigitated electrodes that corresponds to capacitors in parallel.

FIG. 17 gives an example of an interdigitated electrode system that is equivalent to capacitors in parallel, so that the measured capacitance is the sum of the capacitances of the individual capacitors. Thus, the capacitance of the system is much higher than that of an individual capacitor. Furthermore, the small size of the distance between the proximate edges of the adjacent electrodes of opposite sign (electrically oppositely charged) enhances the capacitance of each individual capacitor. An electrode system can be used to sense the load in the region of the system. By using a number of systems positioned in desired locations for load monitoring, the spatial distribution of the load can be sensed. The use of aluminum foil in conjunction with double-sided adhesive tape to make each system facilitates the reconfiguration of the array of systems, in addition to allowing low cost in both materials and installation. Alternate materials such as steel can be used for the electrodes. Alternate materials such as polymeric adhesives can be used for the dielectric film.

Capacitance measurement and electrical resistance measurement are the two main types of electrical measurement. The capacitance method is simpler and less expensive to implement than the resistance method. The resistance method requires electrical contacts with sufficiently low contact electrical resistance, thus necessitating the use of relatively expensive conductive agents (such as silver paint) and the removal of any protective coating prior to the application of the electrical contacts to the cement-based material. Furthermore, reliable measurement of the electrical resistance requires four electrical contacts, with the outer two contacts for passing current and the inner two contacts for measuring the voltage. By using four contacts, the contact resistance essentially does not contribute to the measured resistance. If two contacts are used instead, the contact resistance is included in the measured resistance, thus causing the measured resistance to be not sufficiently indicative of the condition of the cement-based material being inspected. In contrast, capacitance measurement involves only two electrodes (electrical contacts). The two-electrode configuration is much simpler to implement than the four-electrode configuration.

Although preferred embodiments have been depicted and described in detail herein, it will be apparent to those skilled in the relevant art that various additions, substitutions, modifications and the like can be made without departing from the spirit of the invention and these are therefore considered to be within the scope of the invention as defined in the claims which follow.

What is claimed:

1. Cement-based material system for the self-sensing of a force exerted on said cement-based material,
    said force being selected from the group consisting of: compressive force, tensile force, flexural force, shear force, torsional force, and combinations thereof,
    said system comprising electrode A,
    said system also comprising electrode B,
        said electrode A being electrically conductive,
        said electrode B being electrically conductive,
    said system also comprising said cement-based material,
    said cement-based material exhibiting exterior geometric surface,
        said exterior geometric surface being selected from the group consisting of: surface I, surface II, and combinations thereof,
            said surface I being the surface on which the force is exerted,
            said surface II being the surface opposite to surface I,
    said electrode A and said electrode B being positioned on surface S,
        said surface S being selected from the group consisting of: said surface I, and said surface II,
        said electrode A and said electrode B exhibiting proximate edges,
            said edges being separate from one another by a distance,
    said force being exerted on part of said surface I,
        said part being positioned in a part of a region,
        said region extending along a line,
            said line extending from the location of one said edge to the location of the other said edge,
            said line being in the plane of said surface I,
    said electrode A being substantially smaller in area than said surface S,
    said electrode B being substantially smaller in area than said surface S,
    said electrode A and said electrode B being electrically oppositely charged, said being electrically oppositely charged resulting between an applied alternating electric current,
said applied alternating electric current flowing from said electrode A to said electrode B,
said applied alternating electric current flowing in said cement-based material,
said electrode A and said electrode B exhibiting capacitance between them,
said capacitance comprising the capacitance of said cement-based material,
said capacitance ranging from 0.1 pF to 1 μF,
said capacitance serving as an indicator of said force.

2. The cement-based material system of claim 1, wherein said force exhibits direction Q,
said direction Q being perpendicular to said surface I.

3. The cement-based material system of claim 1, wherein said distance ranges from 1 mm to 1 m.

4. The cement-based material system of claim 1, wherein said applied alternating electric current exhibits frequency,
said frequency ranging from 1 Hz to 100 kHz.

5. The cement-based material system of claim 1, wherein said system also comprises dielectric film A,
said system also comprises dielectric film B,
said dielectric film A being positioned between electrode A and said surface S,
said dielectric film B being positioned between electrode B and said surface S,
said dielectric film A being in contact with the entire area of said electrode A,
said dielectric film B being in contact with the entire area of said electrode B,
said dielectric film A being in contact with said surface S, and
said dielectric film B being in contact with said surface S.

6. The cement-based material system of claim 1, wherein said electrode A comprises a plurality of parallel strips A,
all of said parallel strips A being electrically connected,
said electrode B comprises a plurality of parallel strips B,
all of said parallel strips B being electrically connected, and
said parallel strips A and said parallel strips B being interdigitated.

7. The cement-based material system of claim 1, wherein said electrode A comprises material selected from the group consisting of: metal, metal alloy, metal-based material, metal-matrix composite, aluminum, copper, nickel, titanium, steel, electrically conductive polymer, and combinations thereof, and
said electrode B comprises material selected from the group consisting of: metal, metal alloy, metal-based material, metal-matrix composite, aluminum, copper, nickel, titanium, steel, electrically conductive polymer, and combinations thereof.

8. Cement-based material system for weighing,
said weighing being determining weight,
said weight being applied to said cement-based material,
said system comprising electrode A,
said system also comprising electrode B,
said electrode A being electrically conductive,
said electrode B being electrically conductive,
said system also comprising said cement-based material,
said cement-based material exhibiting exterior geometric surface,
said exterior geometric surface being selected from the group consisting of: surface I, surface II, and combinations thereof,
said surface I being the surface on which said weight is applied,
said surface II being the surface opposite to surface I,
said electrode A and said electrode B being positioned on surface S,
said surface S being selected from the group consisting of: said surface I, and said surface II,
said electrode A and said electrode B exhibiting proximate edges,
said edges being separate from one another by a distance,
said weight being applied to part of said surface I,
said part being positioned in a part of a region,
said region extending along line,
said line extending from the location of one said edge to the location of the other said edge,
said line being in the plane of said surface I,
said electrode A being substantially smaller in area than said surface S,
said electrode B being substantially smaller in area than said surface S,
said electrode A and said electrode B being electrically oppositely charged,
said being electrically oppositely charged resulting from an applied alternating electric current,
said applied alternating electric current flowing between said electrode A to said electrode B,
said applied alternating electric current flowing in said cement-based material, said electrode A and said electrode B exhibiting capacitance between them,
said capacitance comprising the capacitance of said cement-based material,
said capacitance ranging from 0.1 pF to 1 μF, and
said capacitance serving as an indicator of said weight.

9. The cement-based material system of claim 8, wherein said distance ranges from 1 mm to 1 m.

10. The cement-based material system of claim 8, wherein said applied alternating electric current exhibits frequency,
said frequency ranging from 1 Hz to 100 kHz.

11. The cement-based material system of claim 8, wherein said system also comprises dielectric film A,
said system also comprises dielectric film B,
said dielectric film A being positioned between electrode A and said surface S,
said dielectric film B being positioned between electrode B and said surface S,
said dielectric film A being in contact with the entire area of said electrode A,
said dielectric film B being in contact with the entire area of said electrode B,
said dielectric film A being in contact with said surface S, and
said dielectric film B being in contact with said surface S.

12. The cement-based material system of claim 8, wherein said electrode A comprises a plurality of parallel strips A,
all of said parallel strips A being electrically connected,
said electrode B comprises a plurality of parallel strips B,
all of said parallel strips B being electrically connected, and said parallel strips A and said parallel strips B being interdigitated.

13. The cement-based material system of claim 8, wherein
said electrode A comprises material selected from the group consisting of: metal, metal alloy, metal-based material, metal-matrix composite, aluminum, copper, nickel, titanium, steel, electrically conductive polymer, and combinations thereof, and
said electrode B comprises material selected from the group consisting of: metal, metal alloy, metal-based material, metal-matrix composite, aluminum, copper, nickel, titanium, steel, electrically conductive polymer, and combinations thereof.

14. A method of the self-sensing of force exerted on a cement-based material,
said force being selected from the group consisting of: compressive force, tensile force, flexural force, shear force, torsional force, and combinations thereof,
said cement-based material exhibiting exterior geometric surface,
said exterior geometric surface being selected from the group consisting of: surface I, surface II, and combinations thereof,
said surface I being the surface on which the force is exerted,
said surface II being the surface opposite to surface I, and
said force being exerted on a part of said surface I,
said method comprising
(a) positioning electrode A and electrode B on surface S,
said surface S being selected from the group consisting of: said surface I, and said surface II,
said electrode A and said electrode B being electrically conductive,
said electrode A and said electrode exhibiting proximate edges,
said edges being separate from one another by a distance,
said force being exerted on a part of said surface I,
said part being positioned in a part of a region,
said region extending along line,
said line extending from the location of one said edge to the location of the other said edge,
said line being in the plane of said surface I,
said electrode A being substantially smaller in area than said surface S,
said electrode B being substantially smaller in area than said surface S,
and
(b) measuring the capacitance between said electrode A and said electrode B,
said capacitance ranging from 0.1 pF to 1 μF, and
said capacitance serving as an indicator of said force.

15. The method of claim 14, wherein
said force exhibits direction,
said direction being perpendicular to said surface I.

16. The method of claim 14, wherein said distance ranges from 1 mm to 1 m.

17. The method of claim 14, wherein
said capacitance exhibits frequency,
said frequency ranging from 1 Hz to 100 kHz.

18. The method of claim 14, wherein
the method also comprises positioning dielectric film A between said electrode A and said surface S, and
the method also comprises positioning dielectric film B between said electrode B and said surface S,
said dielectric film A being in contact with the entire area of said electrode A,
said dielectric film B being in contact with the entire area of said electrode B,
said dielectric film A being in contact with said surface S, and
said dielectric film B being in contact with said surface S.

19. The method of claim 14, wherein
said electrode A comprises a plurality of parallel strips A, all of said parallel strips A being electrically connected,
said electrode B comprises a plurality of parallel strips B, all of said parallel strips B being electrically connected, and
said parallel strips A and said parallel strips B being interdigitated.

20. The method of claim 14, wherein
said electrode A comprises material selected from the group consisting of: metal, metal alloy, metal-based material, metal-matrix composite, aluminum, copper, nickel, titanium, steel, electrically conductive polymer, and combinations thereof, and
said electrode B comprises material selected from the group consisting of: metal, metal alloy, metal-based material, metal-matrix composite, aluminum, copper, nickel, titanium, steel, electrically conductive polymer, and combinations thereof.

* * * * *